(12) United States Patent
Chou et al.

(10) Patent No.: US 11,040,939 B1
(45) Date of Patent: Jun. 22, 2021

(54) N-TRANSFER REAGENT AND METHOD FOR PREPARING THE SAME AND ITS APPLICATION

(71) Applicant: NATIONAL CHENG KUNG UNIVERSITY, Tainan (TW)

(72) Inventors: Ho-Hsuan Chou, Tainan (TW); Guan-Han Lu, Tainan (TW); Hsiao-Chin Hsueh, Tainan (TW); Tzu-Chia Huang, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 17/010,499

(22) Filed: Sep. 2, 2020

(30) Foreign Application Priority Data

Jun. 23, 2020 (TW) .................................. 109121410

(51) Int. Cl.
| | | |
|---|---|---|
| *C07D 317/66* | (2006.01) | |
| *C01B 25/10* | (2006.01) | |
| *C07C 245/18* | (2006.01) | |
| *C07C 245/20* | (2006.01) | |

(52) U.S. Cl.
CPC ............ *C07C 245/20* (2013.01); *C01B 25/10* (2013.01); *C07C 245/18* (2013.01); *C07D 317/66* (2013.01)

(58) Field of Classification Search
None
See application file for complete search history.

(56) References Cited

FOREIGN PATENT DOCUMENTS

CN          108495842 A    9/2018

OTHER PUBLICATIONS

Yao et al. "Dual-Functionalization of Alkynes via Copper-Catalyzed Carbene/Alkyne Metathesis: A Direct Access to the 4-Carboxyl Quinolines" ACS Catalysis, 2016, vol. 6, No. 2, pp. 1024-1027.*

Myers et al., "A Phosphine-Mediated Conversion of Azides into Diazo Compounds," Angew. Chem. Int. Ed., vol. 48, 2009, pp. 2359-2363.
Chou et al., "Conversion of Azides into Diazo Compounds in Water," J. American Chemical Society, vol. 135. 2013, pp. 14936-14939.
TW Examination Report corresponding to TW Application No. 109121410, dated Dec. 8, 2020, 7 pages with English translation.
Ho-Hsuan Chou, Final Report for Ministry of Science and Technology of Taiwan, P.O.C., Nov. 6, 2017.
Genyi M. et al., "Modular click chemistry libraries for functional screens using a diazotizing reagent", Nature, 574, 86-89, 2019.

* cited by examiner

*Primary Examiner* — Joseph R Kosack
(74) *Attorney, Agent, or Firm* — Muncy, Geissler, Olds and Lowe, P.C.

(57) ABSTRACT

Provided are a novel N-transfer reagent and a method for preparing the same and its application. The N-transfer reagent is represented by the following Formula (I):

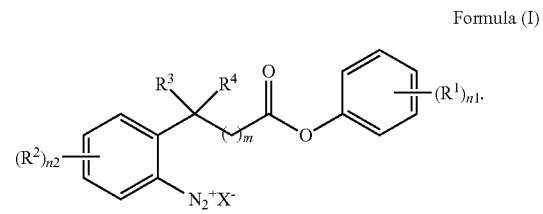

Formula (I)

The various novel N-transfer reagents of the present invention can be quickly prepared by employing different nitrobenzene precursors. The N-transfer reagents can directly convert a variety of amino compounds into diazo compounds under mild conditions. Particularly, the N-transfer reagents can facilitate the synthesis of the diazo compounds. The application of synthesizing diazo compounds of the present invention can greatly decrease the difficulty in operation, increase the safety during experiments, reduce the cost of production and the environmental pollution, and enhance the industrial value of diazo compounds.

19 Claims, No Drawings

N-TRANSFER REAGENT AND METHOD FOR PREPARING THE SAME AND ITS APPLICATION

CROSS-REFERENCE TO RELATED APPLICATION

Pursuant to 35 U.S.C. § 119(a), this application claims the benefit of the priority to Taiwan Patent Application No. 109121410 filed on Jun. 23, 2020. The content of the prior application is incorporated herein by its entirety.

BACKGROUND OF THE INVENTION

1. Field of the Invention

The present invention relates to a nitrogen-transfer reagent (N-transfer reagent) and a method for preparing the same and its application, particularly an N-transfer reagent which directly converts an amino group into a diazo group and a method for preparing the same and its application.

2. Description of the Prior Arts

A diazo compound with a general formula $R_2C=N_2$ is an organic compound with a diazo group. The high reactivity of the diazo compound can facilitate the formation of chemical bonds, so the diazo compound has a broad range of applications in organic synthesis. For example, Bamford-Stevens reaction is used to synthesize alkenes from diazo compounds; Büchner-Curtius-Schlotterbeck reaction is employed to obtain homologated ketones or epoxides by the addition reaction of a diazo compound and an aldehyde or a ketone. The diazo compound can also react with a metal complex such as a copper complex, a rhodium complex, a palladium complex, etc. to generate a metal carbenoid, which can be used to form carbon-hydrogen bonds, carbon-oxygen bonds, or carbon-nitrogen bonds that are not easily established by general chemical reactions.

In addition, the diazo compound can also be applied to the synthesis of medicine, e.g. pyrazole and Trovafloxacin. The pyrazole is an alkaloid and has analgesic, anti-inflammatory, antipyretic as well as sedative effects. It can be prepared by the addition reaction of a diazo compound and an alkene. Trovafloxacin is an antibiotic drug and can be synthesized from ethyl diazoacetate and an alkene. In sum, the diazo compound plays an essential role in the fields of organic synthesis and medicinal chemistry.

Currently, there are many methods to synthesize diazo compounds. However, there are still disadvantages in these methods. For example:

(1) Diazotization of amino compounds: a diazo compound can be obtained by reacting an amino compound with a nitrosonium ion (NO), which is generated in situ from sodium nitrite in an acid condition. The drawback of this method is that the amino compound cannot have any functional group which is unstable under the acidic condition. In addition, the synthesized diazo compound is prone to decompose by eliminating nitrogen gas under the acidic condition, resulting in a certain degree of danger;

(2) Oxidation of hydrazones: a ketone and a hydrazine are first refluxed to undergo a condensation reaction so as to obtain a hydrazone, which is then oxidized into a diazo compound by metal oxides such as silver oxide and mercury oxide. The downside of this method is the usage of the hydrazine, which is toxic and endangers the health of users and the environment;

(3) Basic cleavage of tosylhydrazones: a p-toluenesulfonyl hydrazide and a ketone first undergo a condensation reaction to obtain a tosylhydrazone, which is then converted into a diazo compound under a strong basic condition. The disadvantage of this method is the amino compound cannot have any functional group that is unstable under the basic condition.

The diazo compound has a wide variety of applications and is of great value. However, the current synthetic methods thereof are multi-step reactions and must be performed under strong acid/basic conditions or reacted with toxic reagents, significantly increasing the difficulty in operation and the danger of experiments. In addition, for α-amino acid derivatives that are highly substituted and sterically hindered, converting the amino group thereof into the diazo group with current methods suffers low yields or impossible conversions. Therefore, it is necessary to develop an N-transfer reagent that can directly convert various amino compounds into diazo compounds under mild conditions.

SUMMARY OF THE INVENTION

In view of current process limitations on synthesis of diazo compounds, one of the objectives of the present invention is to provide an N-transfer reagent, which is widely used to synthesize various diazo compounds.

Another objective of the present invention is to optimize the current process of synthesizing diazo compounds and to provide a method that directly converts diverse amino compounds into diazo compounds in a few steps under mild conditions. The method is particularly suitable for synthesizing a diazo compound with at least one sensitive functional group, thereby obtaining a diazo compound that is difficult or even unable to be achieved through current methods.

In order to achieve the above objectives, the present invention provides an N-transfer reagent represented by the following Formula (I):

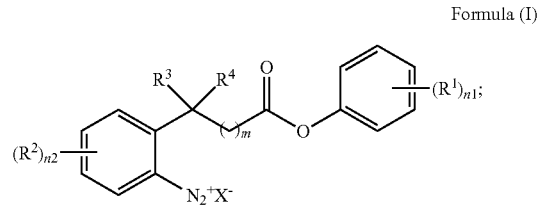

Formula (I)

wherein n1 may be an integer from 0 to 5, and $R^1$ may be selected from the group consisting of: a deuterium atom, a halogen atom, an alkyl group having 1 to 12 carbon atoms, an alkoxy group having 1 to 12 carbon atoms, an aldehyde group having 1 to 12 carbon atoms, a ketone group having 2 to 12 carbon atoms, an ester group having 2 to 12 carbon atoms, an acyloxy group having 2 to 12 carbon atoms, a sulfonic acid group, a sulfonyl group having 1 to 12 carbon atoms, an amide group having 1 to 12 carbon atoms, and an aryl group having 6 to 18 carbon atoms;

wherein n2 may be an integer from 0 to 4, and $R^2$ may be selected from the group consisting of: a deuterium atom, a halogen atom, an alkyl group having 1 to 12 carbon atoms, an alkoxy group having 1 to 12 carbon atoms, an aldehyde group having 1 to 12 carbon atoms, a ketone group having 2 to 12 carbon atoms, an ester group having 2 to 12 carbon atoms, an acyloxy group having 2 to 12 carbon atoms, a polyether group having 3 to 12 carbon atoms, a sulfonic acid group, a sulfonyl group having 1 to 12 carbon atoms, an amide group having 1 to 12 carbon atoms, and an aryl group having 6 to 18 carbon atoms; or when n2 is 2, the two ($R^2$)s are adjacent and connect with each other to form a 1,3-dioxolane group or a 1,4-dioxane group;

wherein $R^3$ and $R^4$ may be each independently selected from the group consisting of: a hydrogen atom, a deuterium atom, and an alkyl group having 1 to 6 carbon atoms;

wherein $X^-$ may be selected from the group consisting of: a hexafluorophosphate anion ($PF_6^-$), a tetrafluoroborate anion ($BF_4^-$), a halogen anion, and a p-toluenesulfonate anion (p-$CH_3C6H_4SO_3^-$); and wherein m may be an integer from 0 to 3.

By using the above-mentioned N-transfer reagent, amino compounds with various functional groups can be directly converted into their corresponding diazo compounds under mild conditions, while the various functional groups remain intact. Therefore, the N-transfer reagent can facilitate synthesis of diazo compounds with diverse functional groups.

Preferably, m may be 1. In an embodiment, m may be 0. In other embodiments, m may also be 2 or 3.

According to the present invention, $R^3$ may be a hydrogen atom, and $R^4$ may also be a hydrogen atom. In an embodiment, $R^3$ and/or $R^4$ may also be an alkyl group having 1 to 6 carbon atoms.

Preferably, $X^-$ may be a hexafluorophosphate anion. According to the present invention, $X^-$ may also be a tetrafluoroborate anion.

According to the present invention, n may be an integer from 1 to 4, and $R^1$ may be a fluorine atom, a chlorine atom, a bromine atom, an iodine atom, a methoxy group, or an acetyl group. In other embodiments, n1 may be an integer from 1 to 3, and R may be a methyl group, an ethyl group, a propyl group, or a butyl group.

According to the present invention, n2 may be an integer from 1 to 3, and $R^2$ may be a fluorine atom, a chlorine atom, a bromine atom, an iodine atom, a methoxy group, an ethoxy group, a methyl ester group, an acetoxy group, an ethylene oxide methyl ether group, a diethylene oxide methyl ether group, or a triethylene oxide ethyl ether group; or n2 may be the integer 2, and the two ($R^2$)s are adjacent and connect with each other to form a 1,3-dioxolane group. By introducing at least one appropriate $R^2$, the stability of the N-transfer reagent is significantly improved, so the N-transfer reagent can be stored at room temperature for a long time. In addition, introducing at least one proper $R^2$ enhances the reactivity of the N-transfer reagent, so the N-transfer reagent can react with various amino compounds to synthesize various diazo compounds successfully.

According to the present invention, the N-transfer reagent may include, but is not limited to, the group consisting of the following:

N-transfer reagent I-1

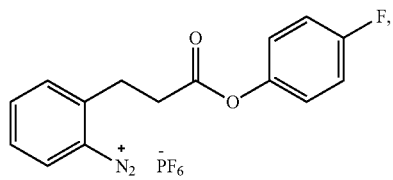

N-transfer reagent I-2

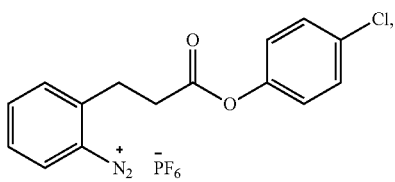

N-transfer reagent I-3

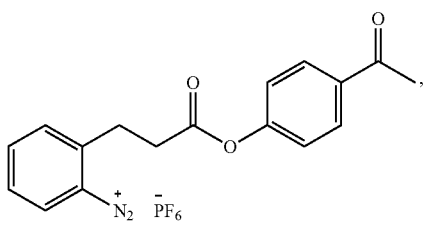

N-transfer reagent I-4

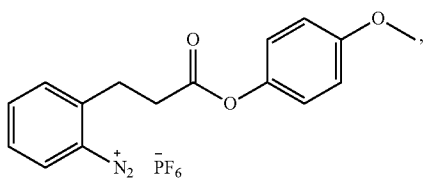

N-transfer reagent I-5

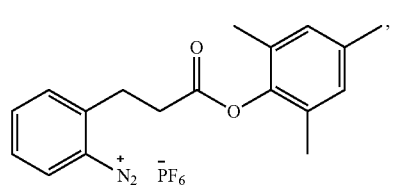

N-transfer reagent I-6

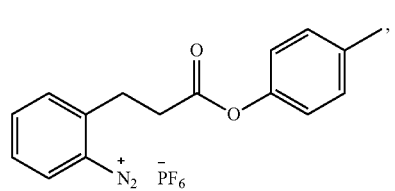

N-transfer reagent I-7

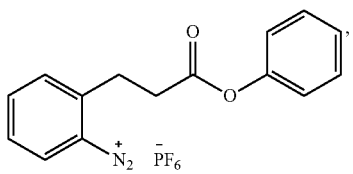

N-transfer reagent I-8

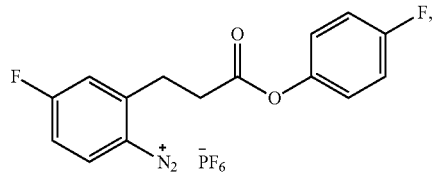

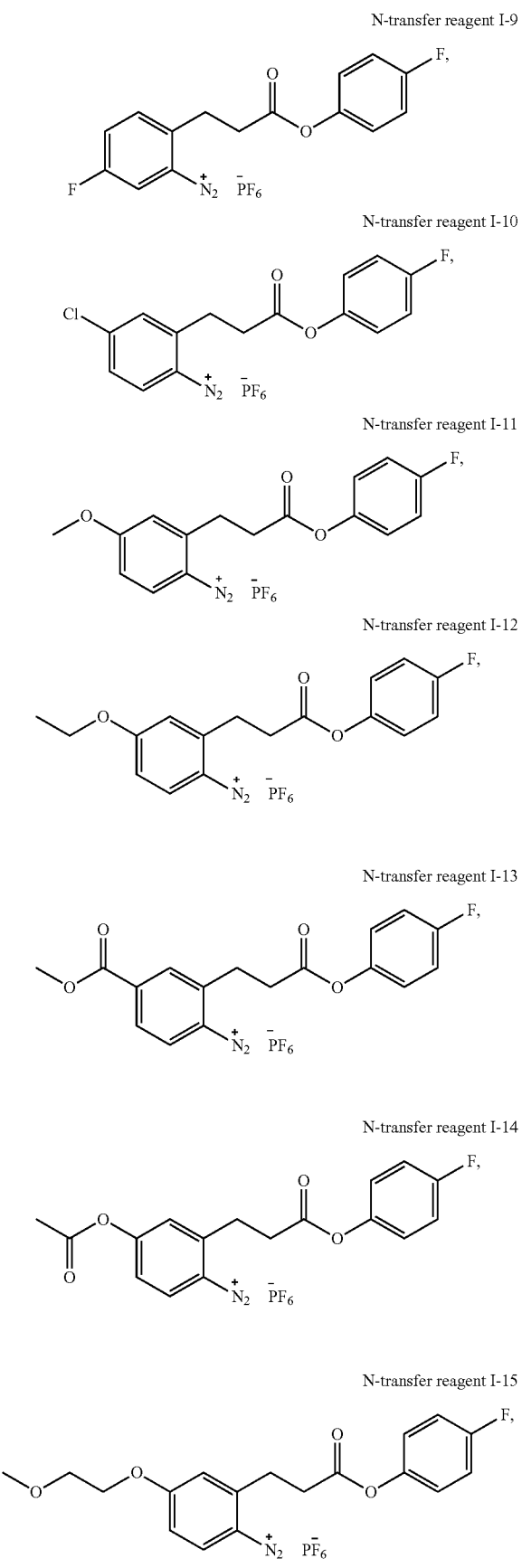
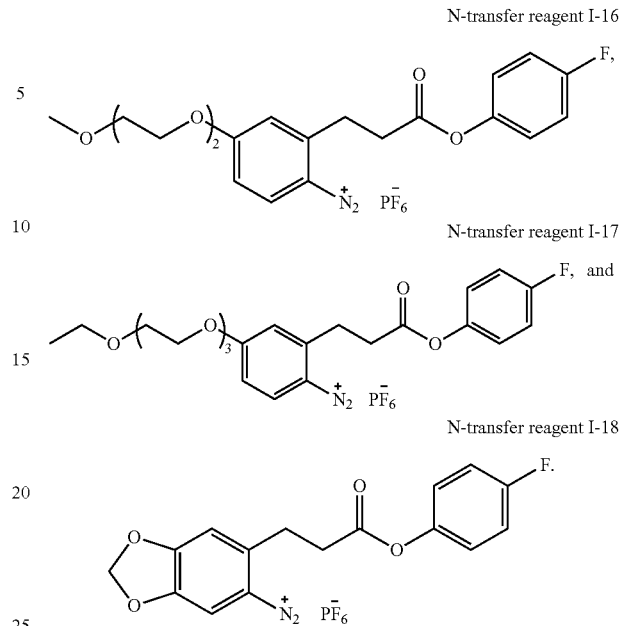

According to the present invention, for the N-transfer reagent, "an ester group" refers to a functional group with the formula "—(C=O)—O—R" connected to a benzene ring, wherein R may be an alkyl group having 1 to 11 carbon atoms. For example, the $R^2$ in the N-transfer reagent I-13 is a methylester group.

According to the present invention, for the N-transfer reagent, "an acyloxy group" refers to a functional group with the formula "—O—(C=O)—R" connected to a benzene ring, wherein R may be an alkyl group having 1 to 1 carbon atoms. For example, the $R^2$ in the N-transfer reagent I-14 is an acetoxy group.

According to the present invention, for the N-transfer reagent, "an amide group having 1 carbon atom" only refers to the functional group with the formula "—(C=O)—NH$_2$" connected to a benzene ring that is, the functional group with the formula "—NH—(C=O)—H" is excluded; "an amide group having 2 to 12 carbon atoms" may refer to a functional group with the formula "—(C=O)—NR'R''" connected to the benzene ring of the N-transfer reagent, wherein one of the R' and R" is a hydrogen atom and the other is an alkyl group having 1 to 11 carbon atoms, or the R' and R" are the same or different alkyl groups and the sum of the carbon atoms thereof may be 2 to 11; "an amide group having 2 to 12 carbon atoms" may also refer to a functional group with the formula "—NH—(C=O)—R" connected to the benzene ring of the N-transfer reagent, wherein R may be an alkyl group having 1 to 11 carbon atoms.

According to the present invention, "an N-transfer reagent" refers to a reagent that can react with an amino compound and directly convert it into a diazo compound by transferring a nitrogen atom from the N-transfer reagent to the amino compound.

The present invention further provides a method for producing the N-transfer reagent. The method comprises the following steps:

step (A): reacting a nitrobenzene precursor represented by the following Formula (II) with a metal catalyst in an atmosphere containing a hydrogen gas to obtain an aniline compound,

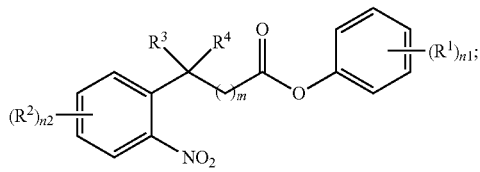

Formula (II)

wherein n1 may be an integer from 0 to 5, and R may be selected from the group consisting of: a deuterium atom, a halogen atom, an alkyl group having 1 to 12 carbon atoms, an alkoxy group having 1 to 12 carbon atoms, an aldehyde group having 1 to 12 carbon atoms, a ketone group having 2 to 12 carbon atoms, an ester group having 2 to 12 carbon atoms, an acyloxy group having 2 to 12 carbon atoms, a sulfonic acid group, a sulfonyl group having 1 to 12 carbon atoms, an amide group having 1 to 12 carbon atoms, and an aryl group having 6 to 18 carbon atoms;

wherein n2 may be an integer from 0 to 4, and $R^2$ may be selected from the group consisting of: a deuterium atom, a halogen atom, an alkyl group having 1 to 12 carbon atoms, an alkoxy group having 1 to 12 carbon atoms, an aldehyde group having 1 to 12 carbon atoms, a ketone group having 2 to 12 carbon atoms, an ester group having 2 to 12 carbon atoms, an acyloxy group having 2 to 12 carbon atoms, a polyether group having 3 to 12 carbon atoms, a sulfonic acid group, a sulfonyl group having 1 to 12 carbon atoms, an amide group having 1 to 12 carbon atoms, and an aryl group having 6 to 18 carbon atoms; or when n2 is 2, the two ($R^2$)s are adjacent and connect with each other to form a 1,3-dioxolane group or a 1,4-dioxane group;

wherein $R^3$ and $R^4$ may be each independently selected from the group consisting of: a hydrogen atom, a deuterium atom, and an alkyl group having 1 to 6 carbon atoms; and wherein m may be an integer from 0 to 3; and step (B): reacting the aniline compound with a nitrosonium ion to undergo diazotization so as to obtain the N-transfer reagent.

By employing the aforesaid method, the N-transfer reagent can be quickly prepared from the nitrobenzene precursor, and the produced N-transfer reagent can be directly applied to the synthesis of different types of diazo compounds.

According to the present invention, the step (B) further comprises:

step (b1): reacting the aniline compound with the nitrosonium ion to undergo diazotization so as to obtain a mixture; and step (b2): purifying the mixture by concentrating, recrystallizing, or a sedimentation method to obtain the N-transfer reagent.

According to the present invention, the method for producing the N-transfer reagent may be performed at a temperature from −15° C. to 25° C.; preferably, the method may be performed at a temperature from −15° C. to 20° C.; more preferably, the method may be performed at a temperature from −15° C. to 10° C.; even more preferably, the method may be performed at a temperature from −15° C. to 5° C.

According to the present invention, the amount of the metal catalyst may be 5% to 20% of the weight of the nitrobenzene precursor; in one embodiment, the amount of the metal catalyst may be 10% to 20% of the weight of the nitrobenzene precursor; in another embodiment, the amount of the metal catalyst may be 15% to 20% of the weight of the nitrobenzene precursor.

According to the present invention, the metal catalyst comprises, but is not limited to, palladium on carbon, a platinum metal, a tin metal, a rubidium metal, a rhodium metal, a ruthenium metal, or an iridium metal.

According to the present invention, the atmosphere may be a pure hydrogen gas or may be a mixture of a hydrogen gas and a nitrogen gas, but is not limited thereto.

According to the present invention, in the step (A), hydrogenation may be processed with polar protic solvents such as methanol or polar aprotic solvents such as tetrahydrofuran (THF).

According to the present invention, in the step (B), the nitrosonium ion may be generated by reacting sodium nitrite with solvents such as acetic acid, hexafluorophosphoric acid, hydrochloric acid, sulfuric acid, perchloric acid, fluoroboric acid, etc., but not limited thereto.

According to the present invention, the step (A) may be performed at room temperature, at a temperature from −10° C. to 10° C., or at a temperature from −5° C. to 5° C.

According to the present invention, the step (B) may be performed at a temperature from −20° C. to 10° C.; preferably, it may be performed at a temperature from −15° C. to 5° C.; more preferably, it may be performed at a temperature from −15° C. to 0° C.

Preferably, the step (A) may be performed in a dark environment.

The present invention further provides an application of the N-transfer reagent, the application comprising: reacting an amino compound and the aforesaid N-transfer reagent with a basic reagent in a solvent to directly convert the amino compound into its corresponding diazo compound.

The application of the N-transfer reagent of the present invention features the following advantages:

(1) Compared with the current harsh conditions for synthesizing diazo compounds, the present invention adopts mild reaction conditions and can greatly reduce the difficulty in operation and ensure the safety during synthesis.

(2) Compared with multiple steps and low yields of the current methods for producing diazo compounds, the application of the present invention can achieve the high yield production of diazo compounds in a few steps.

(3) The application of the present invention can convert a wide variety of compounds with amino groups into diazo compounds without affecting any sensitive functional group of the compounds. Therefore, the application is characterized by chemoselectivity and high synthetic value.

According to the present invention, amino compounds may include ammonium salts, but are not limited thereto.

According to the present invention, the amino compound refers to a compound with at least one primary amino group.

According to the present invention, the amino compound may have, but is not limited to, a functional group or functional groups selected from the group consisting of: a ketone group, a phenyl group, an alkoxy group, an amide group, an ester group, an indole group, an imidazole group, a thioether group, a guanidino group, a hydroxyl group, a phosphonate ester group, and any combination thereof.

According to the present invention, the amino compound and the N-transfer reagent may be reacted at a temperature from −10° C. to 50° C.

According to the present invention, the solvent may be a combination of a protic solvent and an aprotic solvent, and those skilled in the art can adjust the mixing ratio of the two solvents based on their ordinary knowledge. The protic solvent may be, but is not limited to, water, methanol, ethanol, propanol, butanol, or tert-butanol; the aprotic solvent may be, but is not limited to, THF or acetonitrile. Preferably, the solvent may be a mixture of methanol and water, a mixture of THF and water, or a mixture of acetonitrile and water. According to some embodiments, the mixing ratio of the non-aqueous solvent to water may be 0.5:1 to 30:1, preferably 1:1 to 30:1.

According to the present invention, the basic reagent that is suitable for reacting the amino compound with the N-transfer reagent comprises, but is not limited to, potassium carbonate ($K_2CO_3$), potassium bicarbonate ($KHCO_3$), sodium carbonate ($Na_2CO_3$), sodium bicarbonate ($NaHCO_3$), sodium phosphate ($Na_3PO_4$), disodium hydrogen phosphate ($Na_2HPO_4$), potassium phosphate ($K_3PO_4$), dipotassium hydrogen phosphate ($K_2HPO_4$), trimethylamine ($Et_3N$), N,N-diisopropylethylamine (DIPEA), 4-dimethylaminopyridine (DMAP), 1,4-diazabicyclo[2.2.2]octane (DABCO), or 1,8-diazabicyclo[5.4.0]undec-7-ene (DBU).

According to the present invention, the amino compound that is suitable for reacting with the above-mentioned N-transfer reagent includes, but is not limited to, an α-amino ketone, an α-amino amide, an α-amino ester, or an α-amino phosphonate ester. Herein, the "α" position refers to the first carbon atom that attaches to the carbonyl group (C=O) or the phosphoryl group (P=O), and the amino group at the α position is called the "α-amino group".

According to the present invention, the diazo compound may include, but is not limited to, the group consisting of the following:

Diazo compound II-14
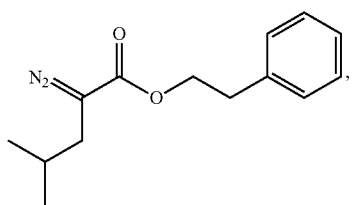
Diazo compound II-15
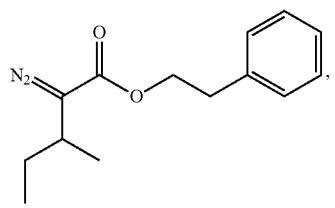
Diazo compound II-16
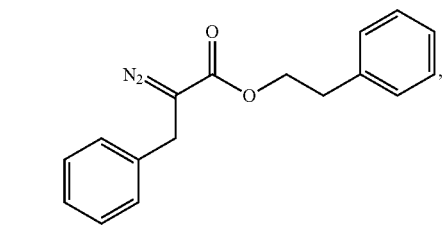
Diazo compound II-17
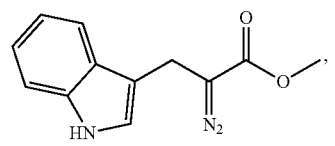
Diazo compound II-18
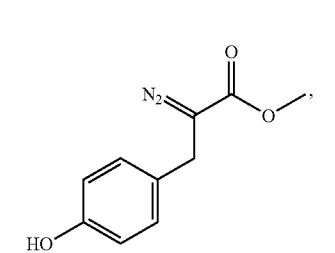
Diazo compound II-19
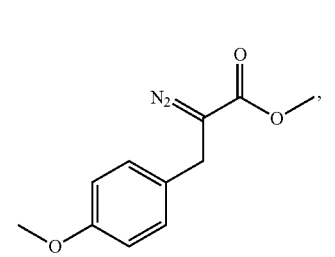
Diazo compound II-20
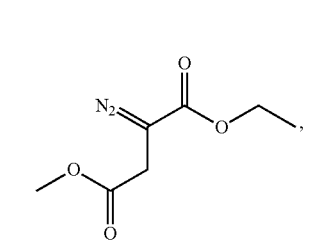
Diazo compound II-21
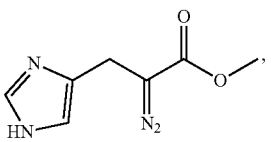
Diazo compound II-22
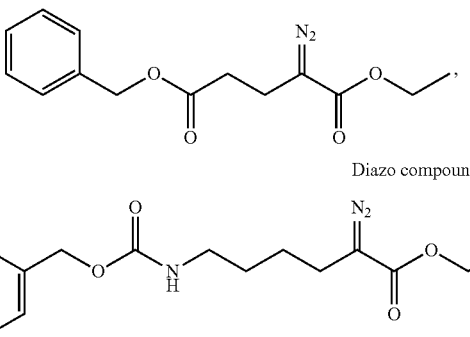
Diazo compound II-23
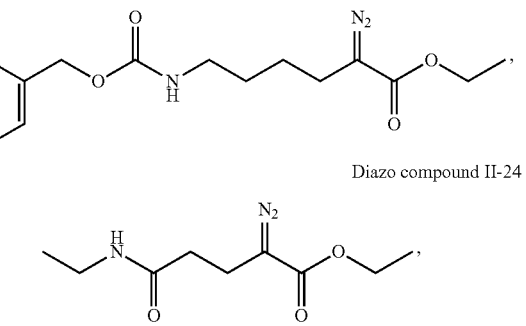
Diazo compound II-24
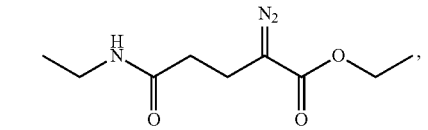
Diazo compound II-25
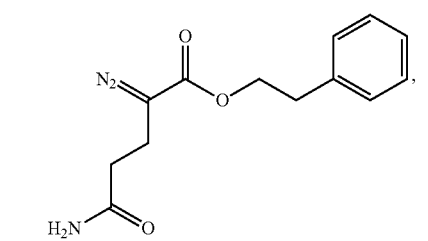
Diazo compound II-26
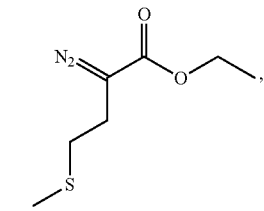
Diazo compound II-27
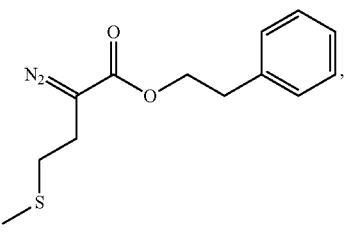

-continued

Diazo compound II-28

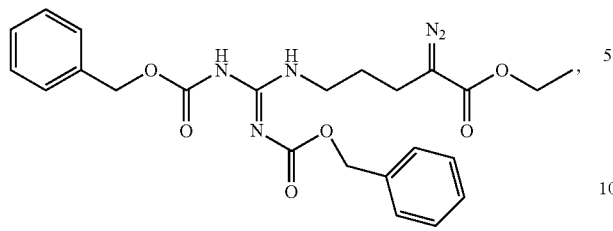

Diazo compound II-29

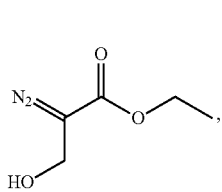

Diazo compound II-30

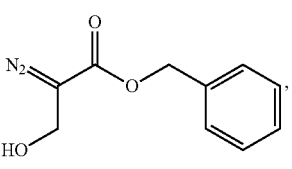

Diazo compound II-31

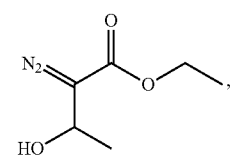

Diazo compound II-32

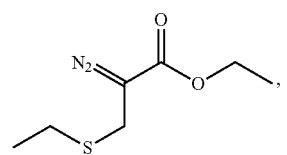

Diazo compound II-33

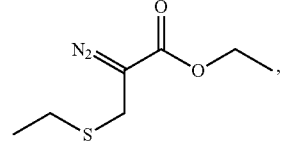 and

Diazo compound II-34

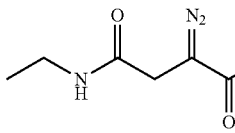

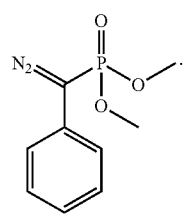

According to the present invention, a ratio of the equivalents of the basic reagent relative to the equivalents of the N-transfer reagent may range from 1:1 to 10:1, preferably, 1:1 to 5:1

BRIEF DESCRIPTION OF THE DRAWINGS

None.

DETAILED DESCRIPTION OF THE PREFERRED EMBODIMENTS

Several examples are exemplified below to illustrate the N-transfer reagent of the present invention and the method for preparing the same and its application so as to highlight the difference between the present invention and the current techniques. It should be understood that the descriptions proposed herein are just preferable examples only for the purpose of illustrations, not intended to limit the scope of the invention. Various modifications and variations could be made in order to practice or apply the present invention without departing from the spirit and scope of the invention.

Synthesis of N-Transfer Reagents

N-transfer reagents (Formula (I)) can be synthesized first by hydrogenation of nitrobenzene precursors (Formula (II)) to obtain aniline compounds (Formula (III)) and followed by diazotization of the aniline compounds. The process is shown below.

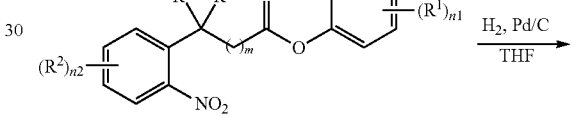

Formula (II)

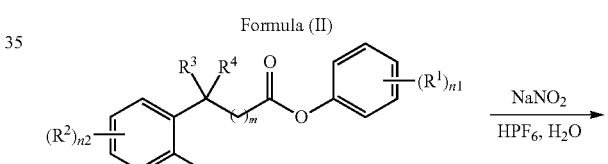

Formula (III)

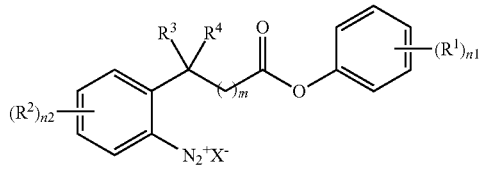

Formula (I)

Herein, the nitrobenzene precursors can be prepared by the following Methods One to Five.

Method One.

Scheme I

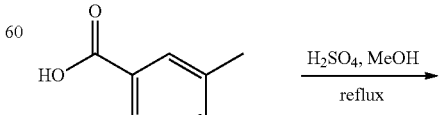

CAS No. 3113-71-1

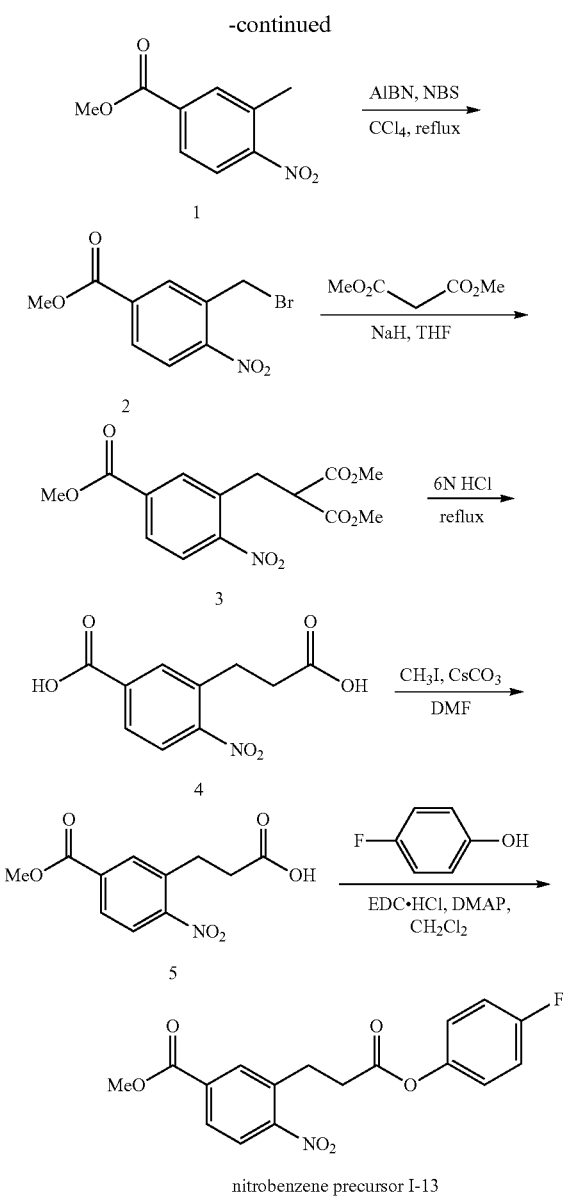

The nitrobenzene precursor I-13 can be prepared by Method One, which is described as follows.

Step 1: Esterification. 3-methyl-4-nitrobenzoic acid (1.0 eq) was dissolved in methanol (0.5 M) at 0° C. to form a suspension, and then concentrated sulfuric acid (H$_2$SO$_4$, 0.7 eq) was added to the suspension carefully. Next, the suspension was refluxed for 5 hours (hr) to obtain a mixture. The mixture was neutralized with 15% aqueous sodium hydroxide (NaOH) and extracted with ethyl acetate (EtOAc) to get rid of organic impurities. Subsequently, the water layer was acidified with 3N hydrochloric acid (HCl) and extracted with EtOAc several times again. The combined organic layers were dried over anhydrous magnesium sulfate (MgSO$_4$), filtered, and then concentrated under reduced pressure to obtain ester 1 without further purification.

Step 2. Benzylic bromination. Azobisisobutyronitrile (AIBN, 0.5 eq) was added to a solution of the ester 1 (1.0 eq), 1-bromosuccinimide (NBS, 1.2 eq), and carbon tetrachloride (CCl$_4$, 1.0 M) to obtain a mixture. The mixture was refluxed for 11 hrs, and the reaction was quenched with water (H$_2$O). The organic and aqueous layers were separated, and the aqueous layer was extracted with dichloromethane (DCM). The combined organic layers were dried over anhydrous MgSO$_4$, filtered, and then concentrated under reduced pressure to obtain a crude product. The crude product was purified by column chromatography to obtain bromide 2.

Step 3. Alkylation with malonic ester. Dimethyl malonate (1.5 eq) was added to a solution of 60% sodium hydride (NaH, 2.0 eq) in THF (0.5 M) in an ice bath under nitrogen to form a mixture, and the mixture was then stirred for 15 minutes (mins). A solution of the bromide 2 in THF (0.8 M) was added to the aforesaid mixture, which was then stirred at 0° C. for another 50 mins. Upon completion, the reaction was quenched with iced water and extracted with EtOAc. The combined organic layers were dried over anhydrous MgSO$_4$, filtered, and then concentrated under reduced pressure to obtain a crude product. The crude product was purified by column chromatography to obtain diester 3.

Step 4. Hydrolysis and decarboxylation. The diester 3 was dissolved in 6N HCl to form a solution, which was then refluxed for 5 hrs. Upon completion, the solution was neutralized with 15% aqueous NaOH and then adjusted to pH 13. Subsequently, the solution was extracted with EtOAc to get rid of organic impurities. The basic aqueous layer was adjusted to pH 2 with 3N HCl and then extracted with EtOAc several times again. The combined organic layers were dried over anhydrous MgSO$_4$, filtered, and then concentrated under reduced pressure to obtain dicarboxylic acid 4.

Step 5. Monomethylation. Cesium carbonate (Cs$_2$CO$_3$, 0.5 eq) and methyl iodide (2.0 eq) were added to a solution of the dicarboxylic acid 4 (1.0 eq) in N,N-dimethylformide (DMF, 0.5 M) to form a mixture. The mixture was stirred at −5° C. for 18 hrs, quenched with water, and then diluted with EtOAc. Subsequently, the mixture was extracted with water-whose volume was ten times the volume of the original DMF to remove the DMF. The organic and aqueous layers were then separated, and the organic layer was dried over anhydrous MgSO$_4$, filtered, and then concentrated under reduced pressure to obtain a crude product. The crude product was purified by column chromatography to obtain monocarboxylic acid 5.

Step 6. Esterification with p-fluorophenol. To a solution of the monocarboxylic acid 5 (1.0 eq) in DCM (0.5 M) were added p-fluorophenol (1.1 eq), 1-ethyl-3-(3-dimethylaminopropyl)carbodiimide hydrochloride (EDC.HCl, 1.1 eq), and 4-dimethylaminopyridine (DMAP catalytic amount) to form a mixture, which was kept stirring at room temperature. Upon completion, the reaction was quenched with water. The organic and aqueous layers were separated, and the aqueous layer was extracted with DCM. The combined organic layers were dried over anhydrous MgSO$_4$, filtered, and then concentrated under reduced pressure to obtain a crude product. The crude product was purified by column chromatography to obtain the nitrobenzene precursor I-13.

Method Two.

Scheme II

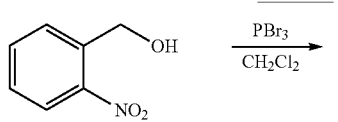

CAS No. 612-25-9

Method Three.

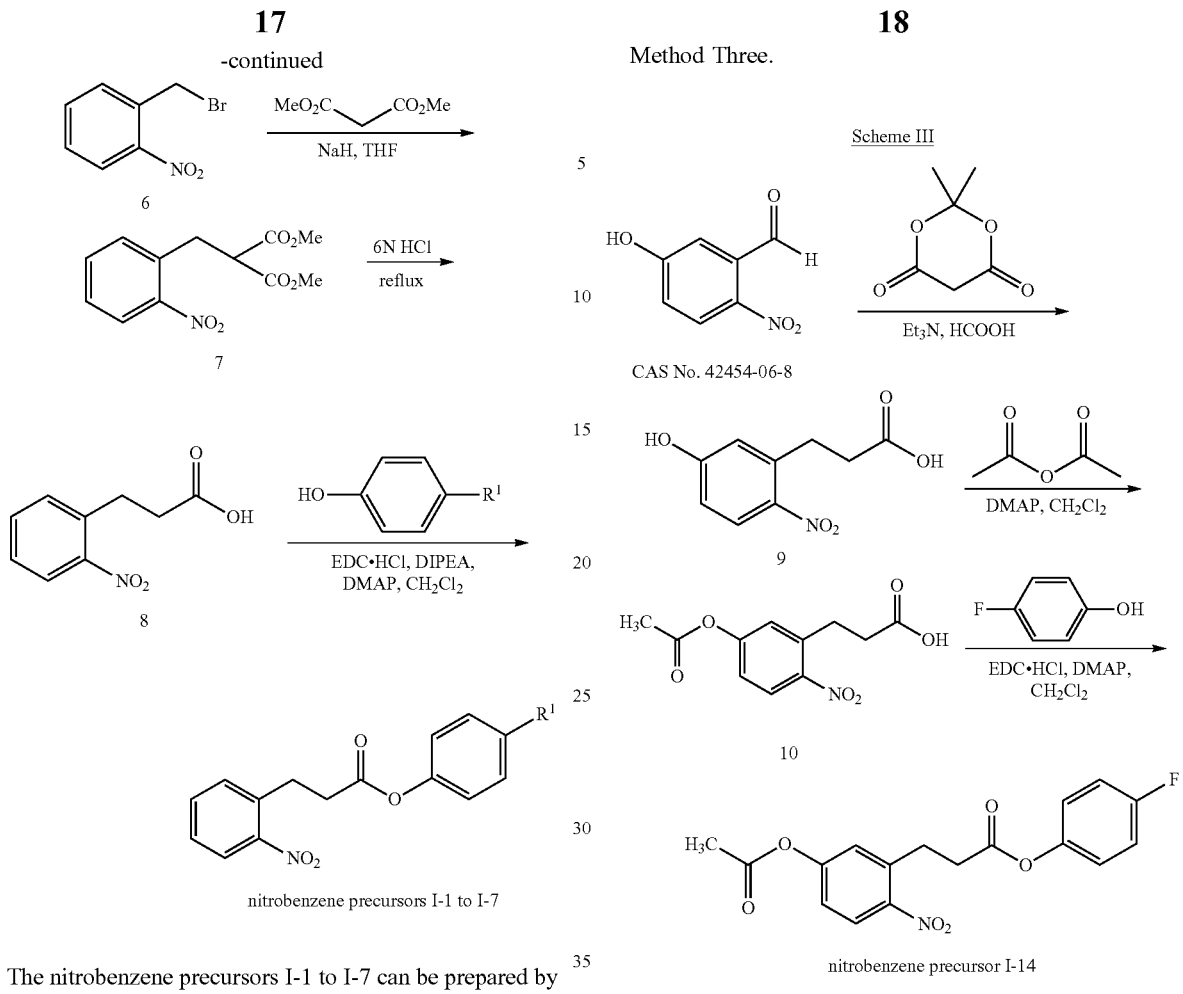

The nitrobenzene precursors I-1 to I-7 can be prepared by Method Two, which is described as follows.

To a solution of 2-nitrobenzyl alcohol in DCM (0.5 M) was added phosphorus tribromide (PBr$_3$, 1.0 eq) at 0° C. to obtain a mixture, which was kept stirring at room temperature for 40 mins. Upon completion, the reaction was quenched with water. The organic and aqueous layers were separated, and the aqueous layer was extracted with DCM. The combined organic layers were dried over anhydrous MgSO$_4$, filtered, and then concentrated under reduced pressure to obtain a crude product. The crude product was purified by column chromatography to obtain bromide 6.

The bromide 6 was used to obtain carboxylic acid 8 according to Steps 3 and 4 of the Method One.

Next, to a solution of the carboxylic acid 8 (1.0 eq) in DCM (0.5 M) were added a phenolic compound (1.1 eq), EDC.HCl (1.1 eq), N,N-diisopropylethylamine (DIPEA, 2.0 eq), and DMAP (catalytic amount) to form a mixture, which was kept stirring at room temperature. Upon completion, the reaction was quenched with water. The organic and aqueous layers were separated, and the aqueous layer was extracted with DCM. The combined organic layers were dried over anhydrous MgSO$_4$, filtered, and then concentrated under reduced pressure to obtain a crude product. The crude product was purified by column chromatography to obtain a nitrobenzene precursor. Herein, the phenolic compounds used to obtain the nitrobenzene precursors I-1 to I-7 are p-fluorophenol, p-chlorophenol, p-acetylphenol, p-methoxyphenol, 2,4,6-trimethylphenol, p-methylphenol, and phenol, respectively.

The nitrobenzene precursor I-14 can be prepared by Method Three, which is described as follows.

Step 1: Condensation with Meldrum's acid. Commercially available 5-hydroxy-2-nitrobenzaldehyde was used as the starting material to synthesize the p-nitrophenol derivative 9 according to *Chemistry—A European Journal* 2014, 20 (22), 6752-6755.

Step 2: Acetylation. To a solution of the p-nitrophenol derivative 9 (1.0 eq) in DCM (0.5 M) were added acetic anhydride (1.1 eq) and DMAP (1.5 eq) to obtain a mixture, which was kept stirring at room temperature. Upon completion, the reaction was quenched with water. The organic and aqueous layers were separated, and the aqueous layer was extracted with EtOAc. The combined organic layers were dried over anhydrous MgSO$_4$, filtered, and then concentrated under reduced pressure to obtain a crude product. The crude product was purified by column chromatography to obtain carboxylic acid 10.

The carboxylic acid 10 was used to obtain the nitrobenzene precursor I-14 according to Step 6 of Method One.

Method Four.

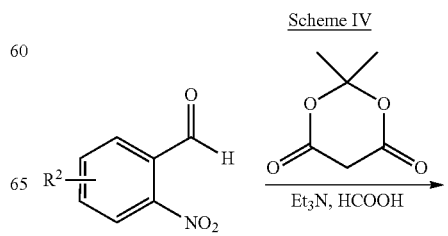

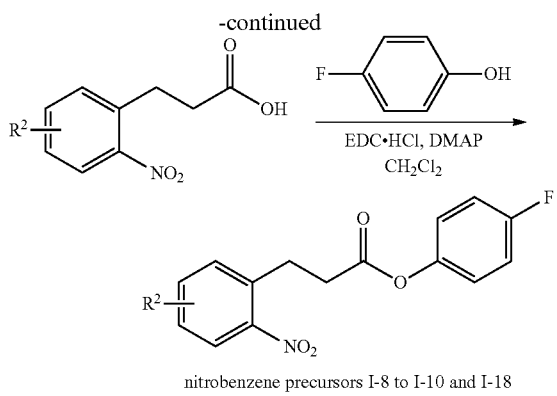

nitrobenzene precursors I-8 to I-10 and I-18

The nitrobenzene precursors I-8 to I-10 and I-18 can be prepared by Method Four, which is described as follows.

The starting materials 5-fluoro-2-nitrobenzaldehyde (CAS No. 395-81-3), 4-fluoro-2-nitrobenzaldehyde (CAS No. 2923-96-8), 5-chloro-2-nitrobenzaldehyde (CAS No. 6628-86-0), and 6-nitropiperonal (CAS No. 712-97-0) were used to synthesize the nitrobenzene precursors I-8, I-9, I-10, and I-18, respectively, according to Step 1 of Method Three and Step 6 of Method One.

Method Five.

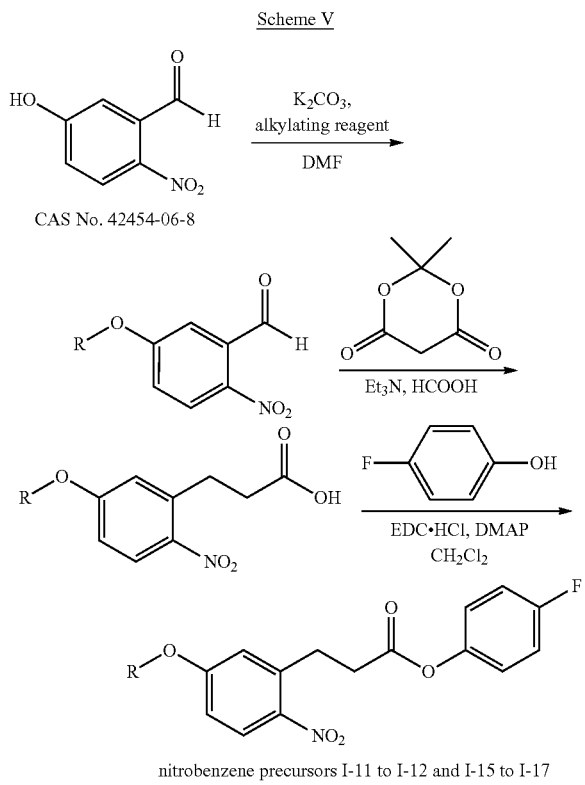

nitrobenzene precursors I-11 to I-12 and I-15 to I-17

The nitrobenzene precursors I-11 to I-12 and I-15 to I-17 can be prepared by Method Five, which is described as follows.

To a solution of 5-hydroxy-2-nitrobenzaldehyde (1.0 eq) in DMF (0.5 M) were added potassium carbonate ($K_2CO_3$, 1.04 eq) and an alkylating reagent (1.0 eq) to form a mixture, which was kept stirring at room temperature. Upon completion, the mixture was diluted with EtOAc. Subsequently, the mixture was extracted with water—whose volume was ten times the volume of the original DMF—to remove the DMF. The organic and aqueous layers were then separated, and the organic layer was dried over saturated aqueous sodium chloride (NaCl) and anhydrous $MgSO_4$, filtered, and then concentrated under reduced pressure to obtain an ether. Herein, the alkylating reagents used to obtain the nitrobenzene precursors I-11 to I-12 and I-15 to I-17 are methyl iodide, ethyl iodide, 2-methoxyethyl tosylate, 2-(2-methoxyethoxy)ethyl tosylate, and triethylene glycol monoethyl ether tosylate, respectively.

The ether was used to synthesize nitrobenzene precursors I-11 to I-12 and I-15 to I-17 according to Step 1 of Method Three and Step 6 of Method One.

N-transfer reagents can be prepared from the nitrobenzene precursors I-1 to I-18 by the following Method I or Method II, both of which are described as follows.

Method I.

Hydrogenation: A flask was charged with an appropriate amount of palladium on carbon (10% Pd/C, whose amount is 10 wt % of the nitrobenzene precursor) and filled with nitrogen gas. THF was added to the flask at 0° C. to form a mixture, to which a solution of certain moles of the nitrobenzene precursor in THF was added. Subsequently, the flask was purged with hydrogen gas to replace the nitrogen gas. The reaction was stirred at 0-4° C. and monitored by thin layer chromatography (TLC). Upon completion, the mixture was filtered through a celite-cotton pad, and the pad was washed with chilly THF. The filtrate containing an aniline compound was kept at −5° C. for diazotization. Herein, the moles of the aniline compound were approximately the same as the moles of the nitrobenzene precursor, i.e. the yield of the hydrogenation was almost 100%.

Diazotization: Sodium nitrite ($NaNO_2$, 1.2 eq) in $H_2O$ (2.0 M) and hexafluorophosphoric acid ($HPF_6$, 1.4 M) were subsequently added into a solution of the aniline compound in THF at −5° C. to obtain a mixture. After 15 mins, the mixture was concentrated under reduced pressure, and the residual concentrate was recrystallized from diethyl ether ($Et_2O$) to obtain a diazonium salt. The diazonium salt was collected by filtration, washed with $Et_2O$, and dried under high vacuum so as to obtain an N-transfer reagent, which was stored under $N_2$ at 0° C.

Method II.

Hydrogenation: A flask was charged with an appropriate amount of 10% Pd/C (whose amount is 15 wt % of the nitrobenzene precursor) and filled with nitrogen gas. THF was added to the flask at −5° C. to form a mixture, to which a solution of certain moles of the nitrobenzene precursor in THF was added. Subsequently, the flask was purged with hydrogen gas to replace the nitrogen gas. The reaction was stirred at −5° C. and monitored by TLC. Upon completion, the mixture was filtered through a celite-cotton pad, and the pad was washed with chilly THF. The filtrate containing an aniline compound was kept at −10° C. for diazotization. Herein, the moles of the aniline compound were approximately the same as the moles of the nitrobenzene precursor, i.e. the yield of the hydrogenation was almost 100%.

Diazotization: Sodium nitrite ($NaNO_2$, 1.2 eq) in $H_2O$ (2.0 M) and $HPF_6$ (1.4 M) were subsequently added into a solution of the aniline compound in THF at −10° C. to obtain a mixture. After 30 mins, the mixture was concentrated under reduced pressure, and the residual concentrate was recrystallized from $Et_2O$ to obtain a diazonium salt. The diazonium salt was collected by filtration, washed with $Et_2O$, and dried under high vacuum so as to obtain an N-transfer reagent, which was stored under $N_2$ at 0° C.

The N-transfer reagents I-1 to I-7 were prepared by Method I from the nitrobenzene precursors I-1 to I-7, while the N-transfer reagents I-8 to I-18 were prepared by Method II from the nitrobenzene precursors I-8 to I-18. The amounts and moles of the nitrobenzene precursors I-1 to I-18 and the amounts, moles, appearances, yields, and characteristics of the synthesized N-transfer reagents I-1 to I-18 are shown in Tables 1 and 2 below.

Applications of the N-Transfer Reagents

The above-mentioned N-transfer reagents can be used to directly convert primary amino groups of various amino compounds into diazo groups, i.e. the aforesaid N-transfer reagents can be used to directly convert diverse amino compounds into their corresponding diazo compounds. The amino compounds that are suitable for the present invention include, but are not limited to, α-amino ketones (e.g. 2-aminoacetophenone hydrochloride, CAS No.: 5468-37-1), α-amino amides, α-amino esters (e.g. L-tryptophan methyl ester hydrochloride, CAS No.: 7524-52-9), or α-amino phosphonate esters (e.g., dimethyl (α-aminobenzyl) phosphonate hydrochloride, CAS No.: 70858-88-7).

40° C. Upon completion, the mixture was diluted with $Et_2O$ and water. The organic and aqueous layers were separated, and the aqueous layer was extracted with $Et_2O$ three times. The combined organic layers were extracted with saturated aqueous NaCl three times to remove DMF, wherein the amount of the saturated aqueous NaCl each time was ten times the volume of the original DMF. Subsequently, the combined organic layers were dried over anhydrous $MgSO_4$, filtered, and then concentrated under reduced pressure to obtain an azide compound.

The azide compound was dissolved in MeOH (5 mL) to form a solution, and a pre-prepared solution of 10% Pd/C in MeOH (2 mL) with TFA (2.0 eq, 336 μL) was added to the aforesaid solution to form a mixture, which was then purged with hydrogen gas. The reaction was stirred at room temperature and monitored by TLC. Upon completion, the mixture was concentrated under reduced pressure to obtain a crude product, and the crude product was washed with DCM to give the amino compound III-2 in a yield of 56%.

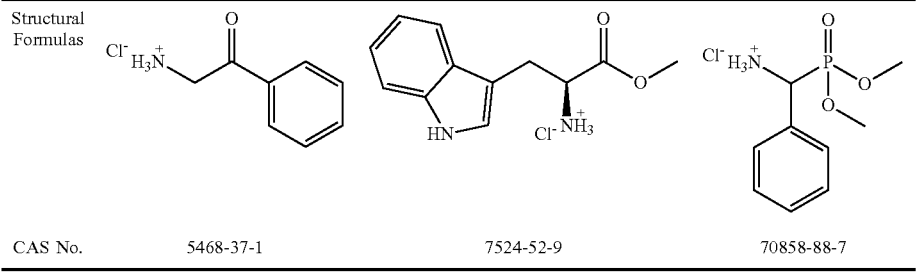

The amino compounds used in the present invention can be prepared by the following Methods One to Eight.

Method One.

Scheme VI

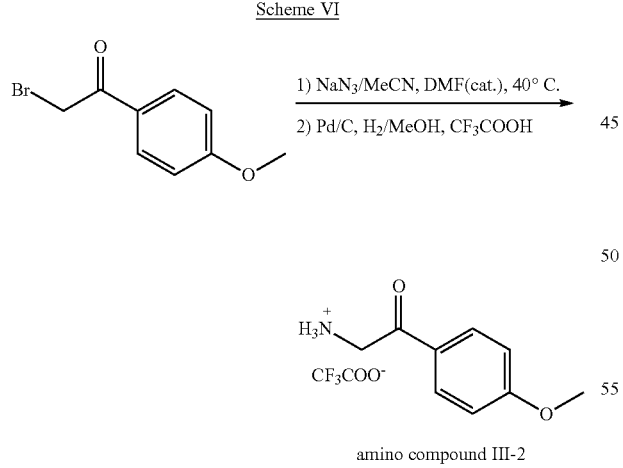

amino compound III-2

The steps for preparing the amino compound III-2 (α-amino ketone) based on Scheme VI are described as follows.

To a solution of 2-bromo-1-(4-methoxyphenyl)-ethan-1-one (1.0 eq, 2.183 mmol) in acetonitrile (10 mL) were added sodium azide ($NaN_3$, 4.138 eq, 9.032 mmol) and DMF (5 mL) to form a mixture, which was kept stirring for 4 hrs at Method Two.

Scheme VII

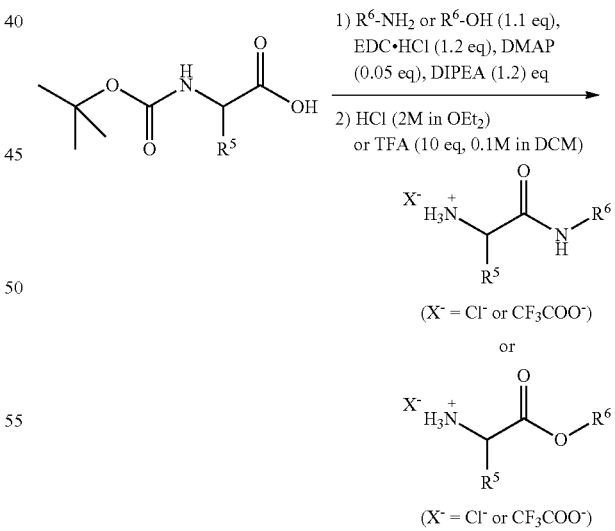

The steps for preparing α-amino amides and α-amino esters based on Scheme VII are described as follows.

To a solution of a commercially available amino acid with Boc (tert-butyloxycarbonyl)-protected amino groups in DCM (1.0 M, since the solubilities of amino acids in DCM vary, the amount of DCM could be increased where applicable) were added a primary amine ($R^6$—$NH_2$) or alcohol ($R^6$—OH) (1.1 eq), EDC.HCl (1.2 eq), DMAP (0.05 eq), and DIPEA (1.2 eq) in order to form a mixture, which was kept stirring at room temperature. Upon completion, the reaction was quenched with water. The organic and aqueous layers were separated, and the aqueous layer was extracted with DCM three times. The combined organic layers were dried over saturated aqueous NaCl and anhydrous $MgSO_4$, filtered, and then concentrated under reduced pressure to obtain a crude product. The crude product was purified by column chromatography with EtOAc in hexane (Hex) or methanol (MeOH) in DCM as eluent to afford a Boc-protected amide or a Boc-protected ester.

The Boc-protected amide or ester was then deprotected with HCl (2M in $Et_2O$) or trifluoroacetic acid (TFA, 10 eq., 0.1M in DCM) to give a desired solid product, which was collected by filtration, washed with $Et_2O$, and dried under high vacuum.

The amino compounds III-3, III-4, III-5, III-9, and III-13 were synthesized according to Scheme VII, wherein the $R^5$ and $R^6$ groups of these amino compounds are shown in Table 3 below.

Method Three.

Scheme VIII

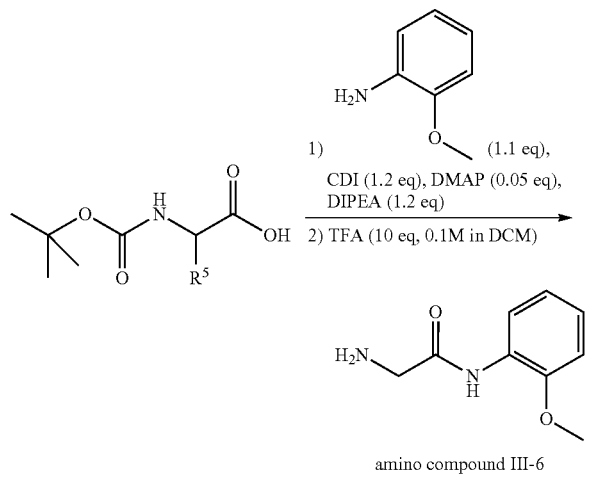

amino compound III-6

The steps for preparing the amino compound III-6 (α-amino amide) based on Scheme VIII are described as follows.

To a solution of commercially available Boc-protected glycine in DCM (1.0 M) were added 2-methoxyaniline (1.1 eq), 1,1'-carbonyldiimidazole (CDI, 1.2 eq), DMAP (0.05 eq), and DIPEA (1.2 eq) in order to form a mixture, which was kept stirring at room temperature. Upon completion, the reaction was quenched with water. The organic and aqueous layers were separated, and the aqueous layer was extracted with DCM three times. The combined organic layers were dried over saturated aqueous NaCl and anhydrous $MgSO_4$, filtered, and then concentrated under reduced pressure to obtain a crude product. The crude product was purified by column chromatography with MeOH in DCM (the volume ratio of MeOH to DCM is 1:19) as eluent to afford a Boc-protected amide.

The Boc-protected amide was dissolved in TFA (10 eq., 0.1M in DCM) to form a solution to de-protect the Boc group. Upon completion, the solution was neutralized with 1 M aqueous NaOH to form a mixture, which was extracted with DCM several times. The combined organic layers were dried over saturated aqueous NaCl and anhydrous $MgSO_4$, filtered, and then concentrated under reduced pressure to obtain the amino compound III-6 in a yield of 75%.

Method Four.

Scheme IX

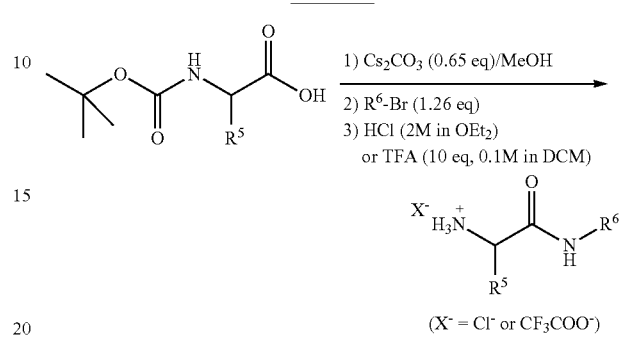

($X^-$ = $Cl^-$ or $CF_3COO^-$)

The steps for preparing α-amino esters based on Scheme IX are described as follows.

Commercially available amino acids with Boc-protected amino groups were used to synthesize the amino compounds III-7, III-8, III-10, III-11, III-12, III-14, III-15, III-16, III-25, III-27, and III-30 based on Scheme IX and according to *The Journal of Organic Chemistry* 2006, 71(16), 6171-6177, wherein the $R^5$ and $R^6$ groups of these amino compounds are shown in Table 3 below.

Method Five.

Scheme X

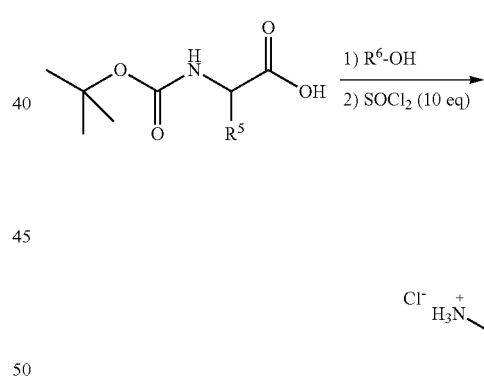

The steps for preparing α-amino esters based on Scheme X are described as follows.

A commercially available Boc-protected amino acid was dissolved in excess alcohols to form a mixture, and thionyl chloride ($SOCl_2$, 10 eq) was then added to the mixture dropwise at 0° C. Subsequently, the temperature was raised to room temperature, and the reaction was kept stirring for several hours. Upon completion, the mixture was concentrated under reduced pressure to obtain the desired product as a pure compound without further purification.

The amino compounds III-18, III-26, and III-29 were synthesized according to Scheme X, wherein the $R^5$ and R groups of these amino compounds are shown in Table 3 below.

Method Six

Scheme XI

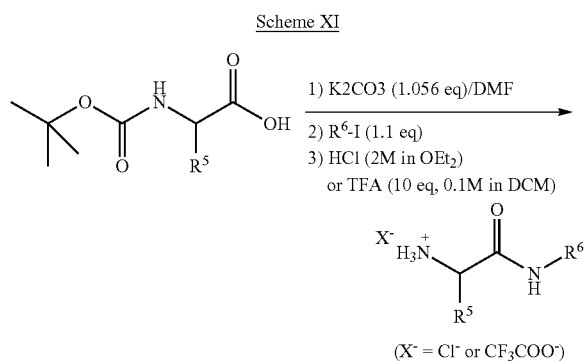

($X^- = Cl^-$ or $CF_3COO^-$)

The steps for preparing α-amino esters based on Scheme XI are described as follows.

Commercially available Boc-protected amino acids and their derivatives thereof were used to synthesize the amino compounds III-19, III-20, III-22, III-23, III-28, III-31, and III-32 based on Scheme XI and according to *Biomacromolecules* 2002, 3(5), 1078-1086, wherein the $R^5$ and $R^6$ groups of these amino compounds are shown in Table 3 below.

Method Seven.

Scheme XII

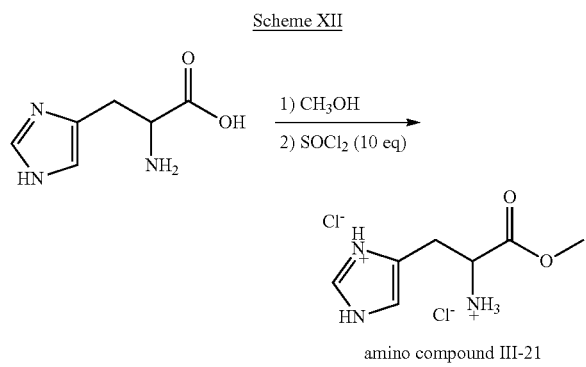

amino compound III-21

The steps for preparing the amino compound III-21 (α-amino ester) based on Scheme XII are described as follows.

Commercially available histidine was dissolved in excess MeOH to form a mixture, and $SOCl_2$ (10 eq) was then added to the mixture dropwise at 0° C. Subsequently, the temperature was raised to room temperature, and the reaction was kept stirring for several hours. Upon completion, the mixture was concentrated under reduced pressure to obtain the amino compound III-21 in a yield of 98% without further purification.

Method Eight.

Scheme XIII

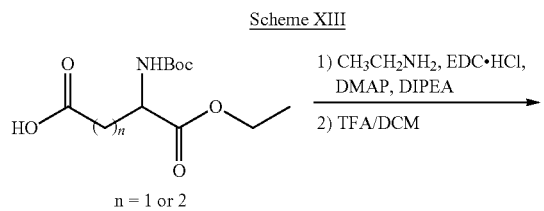

n = 1 or 2

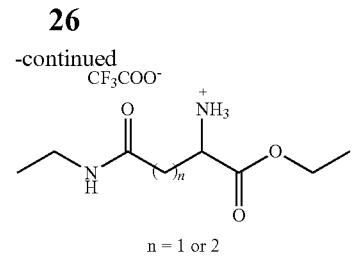

n = 1 or 2

Commercially available Boc-protected glutamic acid monoethyl ester (n=2) and Boc-protected aspartic acid monoethyl ester (n=1) were used as starting materials to synthesize the amino compounds III-24 and III-33 according to the steps of Method Two, and the yields of the amino compounds III-24 and III-33 were 98% and 99%, respectively.

For ease of explanation, the N-transfer reagent I-1 is used as an example to demonstrate how an N-transfer reagent converts the amino compounds listed in Table 4 into diazo compounds.

The process of converting α-amino ketones (CAS No.: 5468-37-1 and the amino compound III-2) into diazo compounds is shown in the following Scheme XIV, wherein $R^7$ can be, but is not limited to, a hydrogen atom, an alkyl group having 1 to 12 carbon atoms, an alkenyl group having 2 to 12 carbon atoms, an alkynyl group having 2 to 12 carbon atoms, a phenyl group having 6 to 18 carbon atoms, an ester group having 2 to 12 carbon atoms, an acyloxy group having 2 to 12 carbon atoms, an amide group having 1 to 12 carbon atoms, or a ketone group having 2 to 12 carbon atoms; $R^8$ can be, but is not limited to, an alkyl group having 1 to 12 carbon atoms, an alkenyl group having 2 to 12 carbon atoms, an alkynyl group having 2 to 12 carbon atoms, or a phenyl group having 6 to 18 carbon atoms; and $X^-$ in the α-amino ketones can be chloride anion ($Cl^-$) or trifluoroacetate anion ($CF_3COO^-$).

Scheme XIV

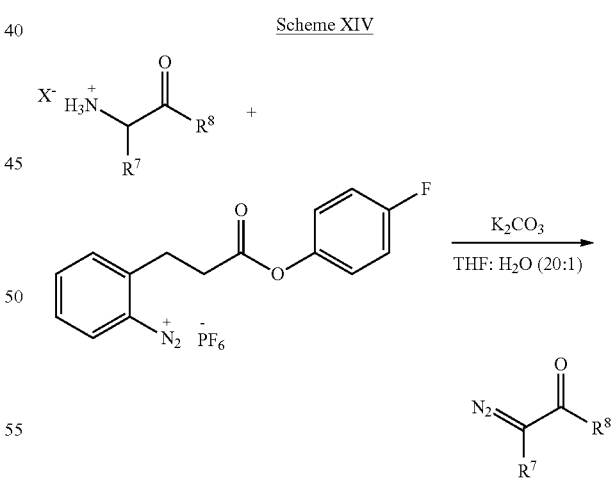

The process of converting α-amino amides (the amino compounds III-3 to III-6) into diazo compounds is shown in the following Scheme XV, wherein $R^9$ can be, but is not limited to, a hydrogen atom, an alkyl group having 1 to 12 carbon atoms, an alkenyl group having 2 to 12 carbon atoms, an alkynyl group having 2 to 12 carbon atoms, a phenyl group having 6 to 18 carbon atoms, an ester group having 2 to 12 carbon atoms, an acyloxy group having 2 to 12 carbon atoms, an amide group having 1 to 12 carbon atoms, or a ketone group having 2 to 12 carbon atoms; $R^{10}$ can be, but is not limited to, a hydrogen atom, an alkyl group having 1 to 12 carbon atoms, or a phenyl group having 6 to 18 carbon atoms; $R^{11}$ can be, but is not limited to, a hydrogen atom, an alkyl group having 1 to 12 carbon atoms, or a phenyl group having 6 to 18 carbon atoms; and $X^-$ in the α-amino amides can be $Cl^-$ or $CF_3COO^-$. The α-amino amides can be not only an amino compound in the form of an ammonium salt (e.g. the amino compounds III-3 to III-5) but also an amino compound with a free primary amino group (e.g. the amino compound III-6).

Scheme XV

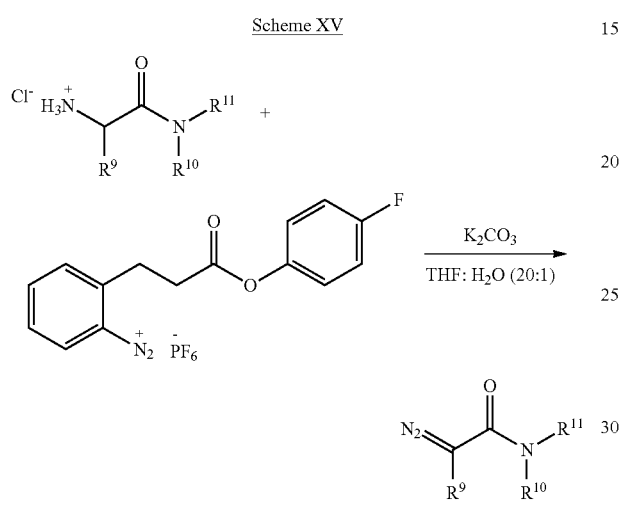

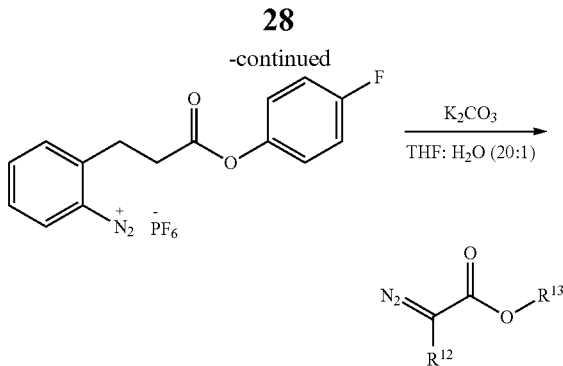

The process of converting α-amino esters (CAS No.: 7524-52-9 and the amino compounds III-7 to III-16 and III-18 to III-33) into diazo compounds is shown in the following Scheme XVI, wherein $R^{12}$ can be, but is not limited to, a hydrogen atom, an alkyl group having 1 to 12 carbon atoms, an alkenyl group having 2 to 12 carbon atoms, an alkynyl group having 2 to 12 carbon atoms, a phenyl group having 6 to 18 carbon atoms, an ester group having 2 to 12 carbon atoms, an acyloxy group having 2 to 12 carbon atoms, an amide group having 1 to 12 carbon atoms, a ketone group having 2 to 12 carbon atoms, side chains of various amino acids, or modified side chains of various amino acids, e.g. a methoxy group that is achieved by modifying an alcohol group in the side chain with a methyl group, an ester group that is achieved by modifying a carboxylic acid group in the side chain with a methyl group or a benzyl group, a Cbz (carboxybenzyl)-modified amino group, an ethyl-modified amide group, an ethyl-modified thiol group, etc.; $R^{13}$ can be, but is not limited to, an alkyl group having 1 to 12 carbon atoms or a phenyl group having 6 to 18 carbon atoms; and $X^-$ in the α-amino esters can be $Cl^-$ or $CF_3COO^-$.

Scheme XVI

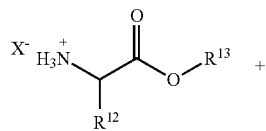

The process of converting an α-amino phosphonate ester (CAS No.: 70858-88-7) into a diazo compound is shown in the following Scheme XVII, wherein $R^{14}$ can be, but is not limited to, a hydrogen atom, an alkyl group having 1 to 12 carbon atoms, an alkenyl group having 2 to 12 carbon atoms, an alkynyl group having 2 to 12 carbon atoms, a phenyl group having 6 to 18 carbon atoms, an ester group having 2 to 12 carbon atoms, an acyloxy group having 2 to 12 carbon atoms, an amide group having 1 to 12 carbon atoms, or a ketone group having 2 to 12 carbon atoms; $R^{15}$ can be, but is not limited to, an alkyl group having 1 to 12 carbon atoms or a phenyl group having 6 to 18 carbon atoms; $R^{16}$ can be, but is not limited to, an alkyl group having 1 to 12 carbon atoms or a phenyl group having 6 to 18 carbon atoms.

Scheme XVII

Each of the processes of Scheme XIV to Scheme XVII is described as follows.

An amino compound was dissolved in a mixture of THF and $H_2O$ at the volume ratio of 20:1 (0.2 M) to form a solution. To the solution was added potassium carbonate ($K_2CO_3$), followed by the N-transfer reagent I-1 at 0° C. After stirring for 15 mins, the temperature was raised to room temperature and monitored by TLC. Upon completion, the solution was diluted with EtOAc and water. The organic and aqueous layers were separated, and the aqueous layer was extracted with EtOAc three times. The combined organic layers were dried over saturated aqueous NaCl and anhydrous $MgSO_4$, filtered, and then concentrated under reduced pressure to obtain a crude product. The crude product was purified by column chromatography with organic eluents to give a diazo compound. Herein, the organic eluents that were used could be EtOAc, Hex, DCM, MeOH, or their combination.

Structural formulas and Chemical Abstracts Service Registry Numbers (CAS No.) or designated numbers of the various amino compounds, equivalents of reactants, composition ratios of eluents, and structural formulas, designated numbers, appearances, and yields of the diazo compounds II-1 to II-34 are shown in Table 4 below, wherein the composition ratios of eluents are shown at a volume ratio of two organic solvents, e.g. "EA/Hex=3:17 v/v" means the eluent is composed of EtOAc and Hex at the volume ratio of 3:17, and wherein when "NMR" is indicated in the yield, it means the yield is calculated from a $^1$H NMR spectrum. The characteristics of the diazo compounds II-1 to II-34 are shown in Table 5 below.

Herein, the N-transfer reagents I-1 to I-7 and I-11 were also used to react with the amino compound III-3 based on substantially the same steps, and the yields of the diazo compound II-3 are shown in Table 6. A person skilled in the art may also choose any other N-transfer reagent, e.g. any one of the N-transfer reagents I-8 to I-10 and I-12 to I-18, to directly convert various amino compounds into their corresponding diazo compounds.

The structures of the N-transfer reagents I-1 to I-18 and the diazo compounds II-1 to II-34 can be confirmed by at least one of the proton nuclear magnetic resonance (H NMR) spectrum, the carbon nuclear magnetic resonance ($^{13}$C NMR) spectrum, the phosphorus nuclear magnetic resonance (P NMR) spectrum, and the mass spectrum thereof. $^1$H, $^{13}$C, and $^{31}$P NMR spectra were recorded on either Bruker Avance III-400 MHz NMR spectrometer or Bruker Avance-500 MHz NMR spectrometers. Deuterated chloroform (CDCl$_3$), deuterated methanol (CD$_3$OD), deuterated acetonitrile (CD$_3$CN), or heavy water (D$_2$O) were used as deuterated solvents. Chemical shifts are reported in parts per million (ppm). When CDCl$_3$ was used, the chemical shift of δ=7.26 ppm (1) was used as an internal standard for $^1$H NMR, and the chemical shift of δ=77.16 ppm (3) was used as an internal standard for $^3$C NMR. When CD$_3$OD was used, the chemical shift of δ=3.30 ppm (δ) was used as an internal standard for $^1$H NMR, the chemical shift of δ=49.00 ppm (7) was used as an internal standard for $^{13}$C NMR, and the calibration steps for $^{31}$P NMR are described as follows: triphenylphosphine (PPh$_3$) was used as a standard to generate a $^{31}$P NMR spectrum and obtain an s.r. value of 70.77, which was used as an instruction for processing data to calibrate chemical shifts of every $^{31}$P NMR spectrum. When CD$_3$CN was used, the chemical shift of δ=1.94 ppm (5) was used as an internal standard for $^1$H NMR, the chemical shift of δ=1.32 ppm (7) was used as an internal standard for $^3$C NMR, and the calibration steps for $^{31}$P NMR was the same as previously stated. When D$_2$O was used, the chemical shift of δ=4.79 ppm (1) was used as an internal standard for $^1$H NMR. The unit of the coupling constant (J) is hertz (Hz). Peak multiplicities are annotated as follows: s, singlet; d, doublet; t, triplet; q, quartet; sext, sextet; sept, septet; nonet; m, multiplet; br, broaden band. Electron Ionization (EI) data were collected on a High Resolution Gas Chromatography Time Of Flight Mass Spectrometer (brand: JEOL; model: AccuTOF GCx-plus). Electrospray Ionization (ESI) data were collected on a High Resolution Orbitrap Mass Spectrometer Tandem Liquid Chromatography and Chip Electrophoresis Analysis System (brand: Thermo Fisher Scientific Inc.; model: Q-Exactive Plus), or a High-Performance Liquid Chromatography Tandem Mass Spectrometer (brand: Varian; Model: VARIAN 901-MS).

TABLE 1

Structural formulas, designated numbers, amounts, and moles of nitrobenzene precursors I-1 to I-18, and structural formulas, designated numbers, amounts, moles, appearances, and yields of synthesized N-transfer reagents I-1 to I-18.

| Nitrobenzene Precursors Structural Formulas | Amount | N-transfer Reagents Structural Formulas | Amount | Appearance | Yield |
|---|---|---|---|---|---|
| Nitrobenzene precursor I-1 (4-F phenyl ester with o-NO$_2$ phenylpropanoate) | 300 mg (1.04 mmol) | N-transfer reagent I-1 (4-F phenyl ester with o-N$_2^+$ PF$_6^-$ phenylpropanoate) | 370 mg (0.89 mmol) | white solid | 86% |
| Nitrobenzene precursor I-2 (4-Cl phenyl ester with o-NO$_2$ phenylpropanoate) | 200 mg (0.65 mmol) | N-transfer reagent I-2 (4-Cl phenyl ester with o-N$_2^+$ PF$_6^-$ phenylpropanoate) | 218 mg (0.50 mmol) | white solid | 77% |
| Nitrobenzene precursor I-3 (4-acetyl phenyl ester with o-NO$_2$ phenylpropanoate) | 400 mg (1.28 mmol) | N-transfer reagent I-3 (4-acetyl phenyl ester with o-N$_2^+$ PF$_6^-$ phenylpropanoate) | 269 mg (0.61 mmol) | white solid | 48% |

TABLE 1-continued

Structural formulas, designated numbers, amounts, and moles of nitrobenzene precursors I-1 to I-18, and structural formulas, designated numbers, amounts, moles, appearances, and yields of synthesized N-transfer reagents I-1 to I-18.

| Nitrobenzene Precursors Structural Formulas | Amount | N-transfer Reagents Structural Formulas | Amount | Appearance | Yield |
|---|---|---|---|---|---|
| Nitrobenzene precursor I-4 | 200 mg (0.66 mmol) | N-transfer reagent I-4 | 250 mg (0.58 mmol) | white solid | 88% |
| Nitrobenzene precursor I-5 | 200 mg (0.64 mmol) | N-transfer reagent I-5 | 216 mg (0.49 mmol) | white solid | 77% |
| Nitrobenzene precursor I-6 | 234 mg (0.82 mmol) | N-transfer reagent I-6 | 135 mg (0.33 mmol) | white solid | 40% |
| Nitrobenzene precursor I-7 | 465 mg (1.72 mmol) | N-transfer reagent I-7 | 627 mg (1.58 mmol) | white solid | 92% |

TABLE 1-continued

Structural formulas, designated numbers, amounts, and moles of nitrobenzene precursors I-1 to I-18, and structural formulas, designated numbers, amounts, moles, appearances, and yields of synthesized N-transfer reagents I-1 to I-18.

| Nitrobenzene Precursors Structural Formulas | Amount | N-transfer Reagents Structural Formulas | Amount | Appearance | Yield |
|---|---|---|---|---|---|
| 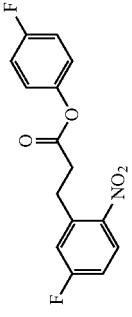<br>Nitrobenzene precursor I-8 | 300 mg (0.98 mmol) | 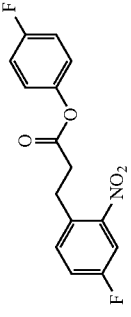<br>N-transfer reagent I-8 | 284 mg (0.65 mmol) | white solid | 66% |
| 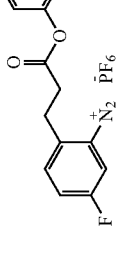<br>Nitrobenzene precursor I-9 | 250 mg (0.81 mmol) | 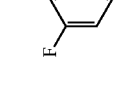<br>N-transfer reagent I-9 | 329 mg (0.76 mmol) | white solid | 94% |
| 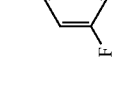<br>Nitrobenzene precursor I-10 | 300 mg (0.93 mmol) | 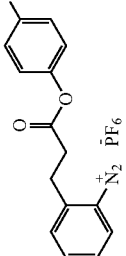<br>N-transfer reagent I-10 | 215 mg (0.48 mmol) | pale orange solid | 52% |
| 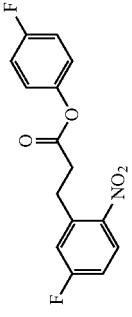<br>Nitrobenzene precursor I-11 | 100 mg (0.31 mmol) | 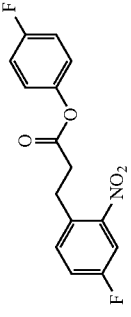<br>N-transfer reagent I-11 | 103 mg (0.23 mmol) | yellow solid | 74% |
| 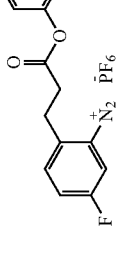<br>Nitrobenzene precursor I-12 | 300 mg (0.90 mmol) | 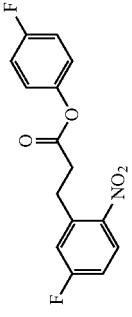<br>N-transfer reagent I-12 | 299 mg (0.65 mmol) | white solid | 72% |

TABLE 1-continued

Structural formulas, designated numbers, amounts, and moles of nitrobenzene precursors I-1 to I-18, and structural formulas, designated numbers, amounts, moles, appearances, and yields of synthesized N-transfer reagents I-1 to I-18.

| Nitrobenzene Precursors Structural Formulas | Amount | N-transfer Reagents Structural Formulas | Amount | Appearance | Yield |
|---|---|---|---|---|---|
| Nitrobenzene precursor I-13 | 60 mg (0.17 mmol) | N-transfer reagent I-13 | 75 mg (0.16 mmol) | white solid | 94% |
| Nitrobenzene precursor I-14 | 300 mg (0.86 mmol) | N-transfer reagent I-14 | 378 mg (0.80 mmol) | purple solid | 93% |
| Nitrobenzene precursor I-15 | 100 mg (0.28 mmol) | N-transfer reagent I-15 | 101 mg (0.21 mmol) | white solid | 75% |
| Nitrobenzene precursor I-16 | 100 mg (0.25 mmol) | N-transfer reagent I-16 | 52 mg (0.10 mmol) | white solid | 40% |

TABLE 1-continued

Structural formulas, designated numbers, amounts, and moles of nitrobenzene precursors I-1 to I-18, and structural formulas, designated numbers, amounts, moles, appearances, and yields of synthesized N-transfer reagents I-1 to I-18.

| Nitrobenzene Precursors Structural Formulas | Amount | N-transfer Reagents Structural Formulas | Amount | Appearance | Yield |
|---|---|---|---|---|---|
| Nitrobenzene precursor I-17 | 140 mg (0.30 mmol) | N-transfer reagent I-17 | 102 mg (0.17 mmol) | brown solid | 57% |
| Nitrobenzene precursor I-18 | 300 mg (0.90 mmol) | N-transfer reagent I-18 | 283 mg (0.61 mmol) | yellow solid | 68% |

TABLE 2

Characteristics of N-transfer reagents I-1 to I-18.

| N-transfer Reagents and Designated No. thereof | Characteristics |
|---|---|
| 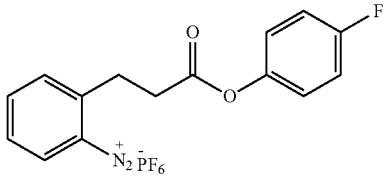<br>N-transfer reagent I-1 | $^1$H NMR (400 MHz, CD$_3$OD, ppm)<br>δ = 8.57 (dd,1 = 8.5, 1.2 Hz, 1H), 8.23 (ddd,1 = 8.6, 7.6, 1.2 Hz, 1H), 8.00 (dd, J = 8.1, 0.7 Hz, 1H), 7.84 (ddd, J = 7.9, 7.9, 1,3 Hz, 1H), 7.12-7.07 (m, 4H), 3.42 (t, J = 6.0 Hz, 2H), 3.24 (t, J = 6.0 Hz, 2H);<br>$^{31}$P NMR (162 MHz, CD$_3$OD, ppm)<br>δ = −144.6 (sept, J$_{P-F}$ = 712.8 Hz). |
| 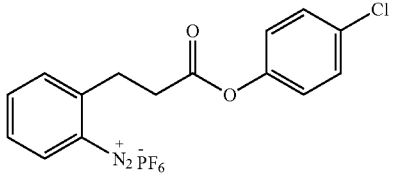<br>N-transfer reagent I-2 | $^1$H NMR (400 MHz, CD$_3$OD, ppm)<br>δ = 8.57 (dd, J = 8.4, 1.3 Hz, 1H), 8.23 (ddd, J = 7.8, 7.8, 1.3 Hz, 1H), 8.00 (dd, J = 8.0, 0.7 Hz, 1H), 7.83 (ddd, J = 8.6, 8.6, 1.1 Hz, 1H), 7.38-7.35 (m, 2H), 7.08-7.06 (m, 2H), 3.43 (d, J = 6.4 Hz, 2H), 3.25 (d, J = 6.4 Hz, 2H);<br>$^{31}$P NMR (162 MHZ, CD$_3$OD, ppm)<br>δ = −144.6 (sept, J$_{P-F}$ = 712.8 Hz). |
| 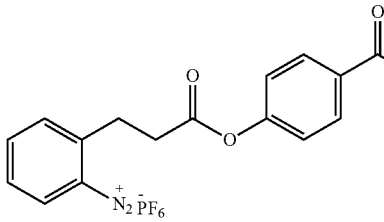<br>N-transfer reagent I-3 | $^1$H NMR (400 MHz, CD$_3$OD, ppm)<br>δ = 8.57 (dd, J = 8.4, 0.9 Hz, 1H), 8.24 (ddd. J = 7.8, 7.8, 1.2 Hz, 1H), 8.04-8.00 (m, 3H), 7.84 (ddd, J = 8.8, 8.8, 0.8 Hz, 1H), 7.23 (d, J = 8.8 Hz, 2H), 3.44 (t , J = 6.4 Hz, 2H), 3.28 (t, = 6.4 Hz, 2H), 2.59 (s, 3H);<br>$^{31}$P NMR (162 MHz, CD$_3$OD, ppm)<br>δ = −144.6 (sept, J$_{P-F}$ = 712.8 Hz). |
| 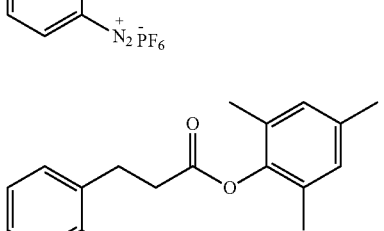<br>N-transfer reagent I-4 | $^1$H NMR (400 MHz, CD$_3$OD, ppm)<br>δ = 8.57 (d, J = 8.3 Hz, 1H), 8.24 (dd, J = 8.3, 8.3 Hz, 1H), 8.00 (d, J = 8.0 Hz, 1H), 7.83 (dd, J = 8.0, 8.0 Hz, 1H), 6.98-6.95 (m,2 H), 6.91-6.89 (m, 2H), 3.78 (s, 3H), 3.42 (t, J = 6.6 Hz, 2H), 3.22 (t, J = 6.6 Hz, 2H);<br>$^{31}$P NMR (162 MHz, CD$_3$OD, ppm)<br>δ = −144.6 (sept, J$_{P-F}$ = 712.8 Hz). |
| 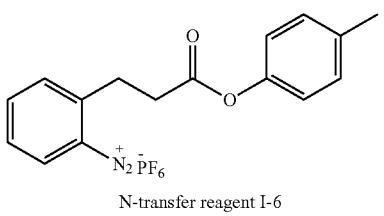<br>N-transfer reagent I-5 | $^1$H NMR (400 MHz, CD$_3$OD, ppm)<br>δ = 8.56 (dd, J = 8.4, 1.3 Hz, 1H), 8.25 (ddd, J = 7.9, 7.9, 1.4 Hz, 1H), 8,04 (dd, J = 7.9, 0.5 Hz, 1H), 7.84 (ddd, J = 8.4, 8.4, 0.9 Hz, 1H), 6.84 (s, 2H), 3.44 (t, J = 6.4 Hz, 2H), 3.31 (t, J = 6.4 Hz, 2H), 2.23 (s, 3H), 1.90 (s, 6H);<br>$^{31}$P NMR (162 MHz, CD$_3$OD, ppm)<br>δ = −144.6 (sept, J$_{P-F}$ = 712.8 Hz). |
| N-transfer reagent I-6 | $^1$H NMR (400 MHz, CD$_3$OD, ppm)<br>δ = 8.56 (dd, J = 8.3. 1.0 Hz, 1H), 8.24 (ddd, J = 7.8, 7.8, 1.3 Hz, 1H), 8.00 (dd, J = 7.8, 1.1 Hz, 1H), 7.83 (ddd = 8.6, 8.6, 1.2 Hz, 1H), 7.16 (d, J = 8.4 Hz, 2H), 6.91 (d, J = 8.4 Hz, 2H), 3.41 (t, J = 6.0 Hz, 2H), 3.22 (t, J = 6.0 Hz, 2H), 2.22 (s, 3H);<br>$^{31}$P NMR (162 MHz, CD$_3$OD, ppm)<br>δ = −144.6 (sept, J$_{P-F}$ = 712.8 Hz). |

TABLE 2-continued

Characteristics of N-transfer reagents I-1 to I-18.

| N-transfer Reagents and Designated No. thereof | Characteristics |
| --- | --- |
| N-Transfer reagent I-7 | $^1$H NMR (400 MHz, CD$_3$OD, ppm) <br> δ = 8.60 (dd, J = 8.4, 1.2 Hz, 1H), 8.28 (ddd, J = 7.9, 7.9, 1.3 Hz, 1H), 8.04 (dd, J = 8.0, 0.6 Hz, 1H), 7.87 (ddd, J = 8.5, 8.5, 1.2 Hz, 1H), 7.43-7.38 (m, 2H), 7.27 (tt, J = 7.6, 1.2 Hz, 1H), 7.10-7.06 (m, 2H), 3.46 (t, J = 6.0 Hz, 2H), 3.28 (t, J = 6.0 Hz, 2H); <br> $^{31}$P NMR (162 MHz, CD$_3$OD, ppm) <br> δ = −144.6 (sept, J$_{P-F}$ = 712.8 Hz). |
| N-Transfer reagent I-8 | $^1$H NMR (400 MHz, CD$_3$OD, ppm) <br> δ = 8.69 (dd, J = 9.2, 4.4 Hz, 1H), 7.86 (dd, J = 9.2, 2.4 Hz, 1H), 7.65 (ddd, J = 9.2, 7.6, 2.4 Hz, 1H), 7.11-7.29 (m, 4H), 3.42 (t, J = 6.8 Hz, 2H), 3.25 (t, J = 6.8 Hz, 2H); <br> $^{13}$C NMR (125 MHz, CD$_3$CN, ppm) <br> δ = 172.3, 170.7 (d, J$_{C-F}$ = 269.0 Hz), 160.3 (d, J$_{C-F}$ = 240.9 Hz), 152.2 (d, J$_{C-F}$ = 12.1 Hz), 147.5 (d, J$_{C-F}$ = 2.1 HZ), 137.5 (d, J$_{C-F}$ = 12.7 Hz), 124.2x2 (d, J$_{C-F}$ = 8.6 Hz), 121.7 (d, J$_{C-F}$ = 25.1 Hz), 119.4 (d, J$_{C-F}$ = 25.2 Hz), 117.0x2 (d, J$_{C-F}$ = 23.6 Hz), 111.7, 33.9, 27.8; <br> $^{31}$P NMR (202.5 MHz, CD$_3$CN, ppm) <br> δ = −146.9 (sept, J$_{P-F}$ = 706.7 Hz); <br> HRMS (ESI+) <br> m/z calculated for C$_{15}$H$_{11}$F$_2$N$_2$O$_2$ [M-PF$_6$]$^+$ = 289.0783, found 289.0778. |
| N-Transfer reagent I-9 | $^1$H NMR (400 MHz, CD$_3$OD, ppm) <br> δ = 8.45 (dd, J = 7.2, 2.8 Hz, 1H), 8.11-8.02 (m, 2H), 7.10-7.09 (m, 4H), 3.41 (t, J = 6.8 Hz, 2H), 3.22 (t, J = 6.8 Hz, 2H); <br> $^{13}$C NMR (125 MHz, CD$_3$CN, ppm) <br> δ = 172.4, 161.1 (d, J$_{C-F}$ = 240.9 Hz), 160.9 (d, J$_{C-F}$ = 252.9 Hz), 147.3 (d, J$_{C-F}$ = 2.1 Hz), 144.4 (d, J$_{C-F}$ = 3.2 Hz), 135.8 (d, J$_{C-F}$ = 8.5 Hz), 131.2 (d, J$_{C-F}$ = 21.4 Hz), 124.2x2 (d, J$_{C-F}$ = 8.6 Hz), 119.4 (d, J$_{C-F}$ = 29.7 Hz), 116.9x2 (d, J$_{C-F}$ = 23.5 Hz), 116.7, 33.9, 27.1; <br> $^{31}$P NMR (202.5 MHz, CD$_3$CN, ppm) <br> δ = −146.9 (sept, J$_{P-F}$ = 707.3 Hz); <br> HRMS (ESI+) <br> m/z calculated for C$_{15}$H$_{11}$F$_2$N$_2$O$_2$ [M-PF$_6$]$^+$ = 289.0783, found 289.0778. |
| N-Transfer reagent I-10 | $^1$H NMR (400 MHz, CD$_3$OD, ppm) <br> δ = 8.56 (d, J = 8.9 Hz, 1H), 8.13 (d, J = 2.0 Hz, 1H), 7.90 (dd, J = 8.8, 2.0 Hz, 1H), 7.11-7.03 (m, 4H), 3.40 (t, J = 6.8 Hz, 2H), 3,24 (t, J = 6.8 Hz, 2H); <br> $^{13}$C NMR (125 MHz, CD$_3$CN, ppm) <br> δ = 172.4, 161.2 (d, J$_{C-F}$ = 241.0 Hz), 149.9, 149.1, 147.4, 134,8, 134.3, 131.4, 124.2x2 (d, J$_{C-F}$ = 8.6 Hz), 117.0x2 (d, J$_{C-F}$ = 23,5 Hz), 114.5, 33.9, 27.6; <br> $^{31}$P NMR (202.5 MHz, CD$_3$CN, ppm) <br> δ = −146.9 (sept, J$_{P-F}$ = 766.3 Hz); <br> HRMS (ESI+) <br> n/z calculated for C$_{15}$H$_{11}$ClFN$_2$O$_2$ [M-PF$_6$]$^+$ = 305.0488, found 305.0480. |
| N-Transfer reagent I-11 | $^1$H NMR. (400 MHz, CD$_3$CN, ppm) <br> δ = 8.30 (d, J = 9.6 Hz, 1H), 7.33 (d, J = 1.6 Hz, 1H), 7,23 (dd, J = 9.6, 1.6 Hz, 1H), 7.16-7.05 (m, 4H), 4.07 (s, 3H), 3.23 (t, J = 6.4 Hz, 2H), 3.13 (t, J = 6.4 Hz, 2H); <br> $^{13}$C NMR (125 MHz, CD$_3$CN, ppm) <br> δ = 172.3, 171.1, 161.2 (d, J$_{C-F}$ = 240.9 Hz), 151.1, 147.5, 136.6, 124.2x2 (d, J$_{C-F}$ = 8.6 Hz), 119.2, 117.7, 116.9x2 (d, J$_{C-F}$ = 23.6 Hz), 103.3, 58.5, 34.1, 27.6; <br> $^{31}$P NMR (202.5 MHz. CD$_3$CN, ppm) <br> δ = −146.9 (sept, J$_{P-F}$ = 706.7 Hz); <br> HRMS (ESI+) <br> m/z calculated for C$_{16}$H$_{11}$F$_2$N$_2$O$_3$ [M-PF$_6$]$^+$ = 301.0983, found 301.0977. |

TABLE 2-continued

Characteristics of N-transfer reagents I-1 to I-18.

| N-transfer Reagents and Designated No. thereof | Characteristics |
|---|---|
| N-Transfer reagent I-12 | $^1$H NMR (400 MHz, CD$_3$CN, ppm)<br>δ = 8.29 (d, J = 9.6 Hz, 1H), 7.29 (d, J = 2.0 Hz, 1H), 7.19 (dd, J = 9.6, 2.0 Hz, 1H), 7.16-7.05 (m, 4H), 4.35 (q, J = 7.2 Hz, 2H), 3.22 (t, J = 6.0 Hz, 2H), 3.12 (t, J = 6.0 Hz, 2H), 1.45 (t, J = 7.2 Hz, 3H);<br>$^{13}$C NMR (125 MHz, CD$_3$CN, ppm)<br>δ = 172.3, 170.5, 161.2 (d, $J_{C-F}$ = 240.9 Hz), 151.1, 147.5, 136.6. 124.2x2 (d, $J_{C-F}$ = 5 Hz), 119.5, 118.0, 117.0x2 (d, $J_{C-F}$ = 23.6 Hz), 102.9, 67.6, 34.1, 27.6, 14.4;<br>$^{31}$P NMR (202.5 MHz, CD$_3$CN, ppm)<br>δ = −146.9 (sept, $J_{P-F}$ = 707.1 Hz);<br>HRMS (ESI+)<br>m/z calculated for C$_{17}$H$_{16}$FN$_2$O$_3$ [M-PF$_6$]$^+$ = 315.1139, found 315.1133. |
| N-Transfer reagent I-13 | $^1$H NMR (400 MHz, CD$_3$CN, ppm)<br>δ = 8.47 (d, J = 8.6 Hz, 1H), 8.41 (d, J = 1.3 Hz, 1H), 8.23 (dd, J = 8.7, 1.6 Hz, 1H), 7.15-7.08 (m, 2H), 7.06-7.02 (m, 2H), 3.97 (s, 3H), 3.35 (t, J = 6.2 Hz, 2H), 3.15 (t, J = 6.2 Hz, 2H);<br>$^{13}$C NMR (125 MHz, CD$_3$CN, ppm)<br>δ = 172.6, 164.7, 161.3 (d, $J_{C-F}$ = 240.8 Hz), 147.9, 142.1, 134.2, 133.9, 130.9, 124.3x2 (d, $J_{C-F}$ = 8 Hz), 120.1, 117.1x2 (d, $J_{C-F}$ = 23.6 Hz), 116.7, 54.3, 34.1, 27.9;<br>$^{31}$P NMR (202.5 MHz, CD$_3$CN, ppm)<br>δ = −145.0 (sept, $J_{P-F}$ = 766.7 Hz);<br>HRMS (ESI+)<br>m/z calculated for C$_{17}$H$_{14}$FN$_2$O$_4$ [M-PF$_6$]$^+$ = 329.0929, found 329.0925. |
| N-Transfer reagent I-14 | $^1$H NMR (400 MHz, CD$_3$OD, ppm)<br>δ = 8.62 (d, J = 9.2 Hz., 1H), 7.84 (d, J = 2.0 Hz, 1H), 7.68 (dd, J = 9.2, 2.0 Hz, 1H), 7.10-7.08 (m, 4H), 4.41 (t, J = 6.4 Hz, 2H), 3.23 (t, J = 6.4 Hz, 2H), 2.39 (s, 3H);<br>$^{13}$C NMR (125 MHz, CD$_3$CN, ppm)<br>δ = 172.3, 168.7, 161.2 (d, $J_{C-F}$ = 241.0 Hz), 150.3, 147.4, 135.8, 126.9, 124.7, 124.2x2 (d, $J_{C-F}$ = 8.6 Hz), 116.9x2 (d, $J_{C-F}$ = 23.6 Hz), 111.5, 33.9, 277, 21.3;<br>$^{31}$P NMR (202.5 MHz, CD$_3$CN, ppm)<br>δ = −146.9 (sept, $J_{P-F}$ = 707.3 Hz);<br>HRMS (ESI+)<br>m/z calculated for C$_{17}$H$_{14}$FN$_2$O$_4$ [M-PF$_6$]$^+$ = 329.0932, found 329.0925. |
| N-Transfer reagent I-15 | $^1$H NMR (400 MHz, CD$_3$CN, ppm)<br>δ = 8.29 (d, J = 9.6 Hz, 1H), 7.33 (d, J = 2.4 Hz, 1H), 7.22 (dd, J = 9.6, 2.4 Hz, 1H), 7.16-7.05 (m, 4H), 4.41-4.39 (m, 2H), 3.77-3.75 (m, 2H), 3.37 (s, 3H), 3.22 (t, J = 6.6 Hz, 2H), 3.12 (t, J = 6.8 Hz, 2H);<br>$^{13}$C NMR (125 MHz, CD$_3$CN, ppm)<br>δ = 172.4, 170.5, 161.3 (d, $J_{C-F}$ = 240.9 Hz), 151.1, 147.6 (d, $J_{C-F}$ = 2.1 Hz), 136.7, 124.3x2 (d, $J_{C-F}$ = 8.6 Hz), 119.8, 118.1, 117.1x2 (d, $J_{C-F}$ = 23.6 Hz), 103.5, 71.0, 70.9, 59.2, 34.2, 27.7;<br>$^{31}$P NMR (202.5 MHz, CD$_3$CN, ppm)<br>δ = −145.0 (sept, $J_{P-F}$ = 706.7 Hz);<br>HRMS (ESI+)<br>m/z calculated for C$_{18}$H$_{18}$FN$_2$O$_4$ [M-PF$_6$]$^+$ = 345.1245; found 345.1235. |

TABLE 2-continued

Characteristics of N-transfer reagents I-1 to I-18.

| N-transfer Reagents and Designated No. thereof | Characteristics |
|---|---|
| 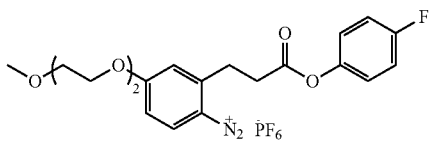<br>N-Transfer reagent I-16 | $^1$H NMR (400 MHz, CD$_3$CN, ppm)<br>δ = 8.29 (d, J = 9.2 Hz, 1H), 7.34 (d, J = 2.4 Hz, 1H), 7.23 (dd, J = 9.2, 2.4 Hz, 1H), 7.16-7.05 (m, 4H), 4.42-4.40 (m, 2H), 3.86-3.84 (m, 2H), 3.64-3.62 (m, 2H) 3.49-3.47 (m, 2H), 3.28 (s, 3H), 3.22 (t, J = 6.8 Hz, 2H), 3.13 (t, J = 6.8 Hz, 2H);<br>$^{13}$C NMR (125 MHz, CD$_3$CN, ppm)<br>δ = 112.4, 170.5, 161.3 (d, J$_{C-F}$ = 240.8 Hz), 151.1, 147.6 (d, J$_{C-F}$ = 2.1 Hz), 136.7 124.3x2 (d, J$_{C-F}$ = 8.6 Hz), 119.8, 118.1, 117.1x2 (d, J$_{C-F}$ = 23.6 Hz), 103.5, 72.5, 71.3, 71.2, 69.5, 58.9, 34.2, 27.7;<br>$^{31}$P NMR (202.5 MHz, CD$_3$CN, ppm)<br>δ = -145.0 (sept, J$_{P-F}$ = 706.7 Hz);<br>HRMS (ESI+)<br>m/z calculated for C$_{20}$H$_{22}$FN$_2$O$_5$ [M-PF$_6$]$^+$ = 389.1507, found 389.1496. |
| 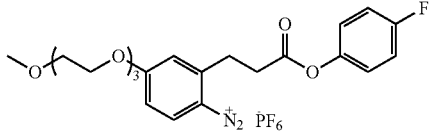<br>N-Transfer reagent I-17 | $^1$H NMR (400 MHz, D$_2$O, ppm)<br>δ = 8.45 (d, J = 9.6 Hz, 1H), 7.44 (d, J = 2.4 Hz, 1H), 7.32 (dd, J = 9.6, 2.4 Hz, 1H), 7.21-7.06 (m, 4H), 4.49 (t, J = 4.4 Hz, 2H), 3.99 (t, J = 4.4 Hz, 2H), 3.80-3.70 (m, 4H), 3.67-3.62 (m, 4H), 3.57 (q, J = 7.2 Hz, 2H), 3.37 (t, J = 6.4 Hz, 2H), 3.28 (t, J = 6.4 Hz, 2H), 1.16 (t, J = 7.2 Hz, 3H);<br>$^{13}$C NMR (125 MHz, CD$_3$OD, ppm)<br>δ = 173.0, 170.9, 161.8 (d, J$_{C-F}$ = 241.3 Hz), 151.4, 147.9, 137.0. 124.3x2 (d, J$_{C-F}$ = 8.5 Hz), 119.7, 118.3, 116.9x2 (d, J$_{C-F}$ = 23.4 Hz), 104.4, 71.8, 71.6x2, 71.2, 70.9, 70.1, 57.6, 34.4, 27.9, 15.4;<br>HRMS (ESI+)<br>m/z calculated for C$_{23}$H$_{28}$FN$_2$O$_6$ [M-PF$_6$]$^+$ = 447.1926, found 447.1914. |
| 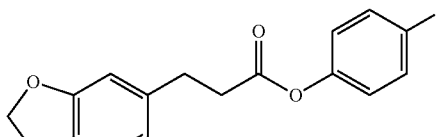 | $^1$H NMR (400 MHz, CD$_3$CN, ppm)<br>δ = 7.57 (s, 1H), 7.26 (s, 1H), 7.18-7.05 (m, 4H), 6.35 (s, 2H), 3.19 (t, J = 6.4 Hz, 2H), 3.08 (t, J = 6.4 Hz, 2H);<br>$^{13}$C NMR (125 MHz, CD$_3$CN, ppm)<br>δ = 172.1, 161.4, 161.1 (d, J$_{C-F}$ = 240.7 Hz), 150.1, 149.2, 147.4, 124.2x2 (d, J$_{C-F}$ = 8.6 Hz), 116.9x2 (d, J$_{C-F}$ = 23.6 Hz), 112.6, 108.7, 107.1, 103.8, 33.9, 27.8;<br>$^{31}$P NMR (202.5 MHz, CD$_3$CN, ppm)<br>δ = -146.9 (sept, J$_{P-F}$ = 706.7 Hz);<br>HRMS (ESI+)<br>m/z calculated for C$_{16}$H$_{12}$FN$_2$O$_4$ [M-PF$_6$]$^+$ = 315.0775, found 315.0768. |

TABLE 3

Methods, starting materials, R5 and R6 groups, and yields for preparing amino compounds III-3 to III-5 III-7 to III-16, III-18 to III-20, III-22 to III-23, and III-25 to 111-32.

| Method | Starting Material | R$^5$ | R$^6$ |
|---|---|---|---|
| Two | Boc-Glycine | 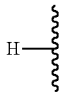 | 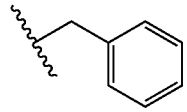 [SMILES: *Cc1ccccc1] |
| Two | Boc-Glycine | 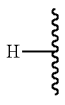 | 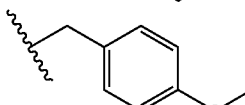 |
| Two | Boc-Glycine | 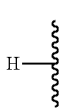 | 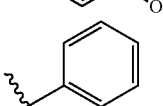 |

TABLE 3-continued

Methods, starting materials, R5 and R6 groups, and yields for preparing amino compounds
III-3 to III-5 III-7 to III-16, III-18 to III-20, III-22 to III-23, and III-25 to 111-32.

| | | | |
|---|---|---|---|
| Four | Boc-Glycine |  | 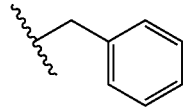 [SMILES: *Cc1ccccc1] |
| Four | Boc-Glycine |  | 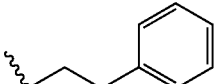 |
| Two | Boc-Alanine |  | 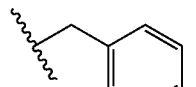 |
| Four | Boc-Alanine |  | 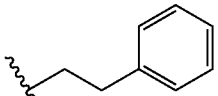 |
| Four | Boc-Valine |  | 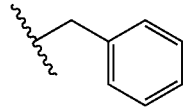 [SMILES: *Cc1ccccc1] |
| Four | Boc-Valine |  | 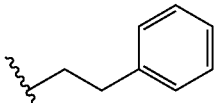 |
| Two | Boc-Leucine | 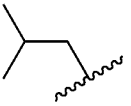 | 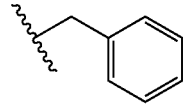 [SMILES: *Cc1ccccc1] |
| Four | Boc-Leucine | 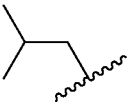 [SMILES: *CC(C)C] | 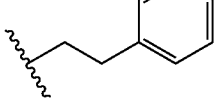 |
| Four | Boc-Isoleucine | 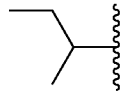 [SMILES: *C(C)CC] | 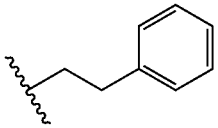 [SMILES: *CCc1ccccc1] |
| Four | Boc-Phenylalanine | 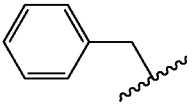 [SMILES: *Cc1ccccc1] | 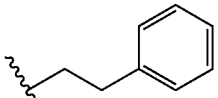 |
| Five | Boc-Tyrosine | 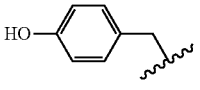 |  |
| Six | Phenol methylated Boc-Tyrosine | 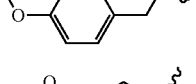 |  |
| Six | Boc-Aspartic acid with mono methyl ester | 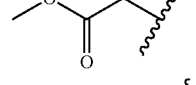 |  |
| Six | Boc-Cautatnic acid with mono benzyl ester | 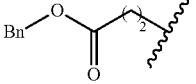 |  |

TABLE 3-continued
Methods, starting materials, R5 and R6 groups, and yields for preparing amino compounds
III-3 to III-5 III-7 to III-16, III-18 to III-20, III-22 to III-23, and III-25 to 111-32.
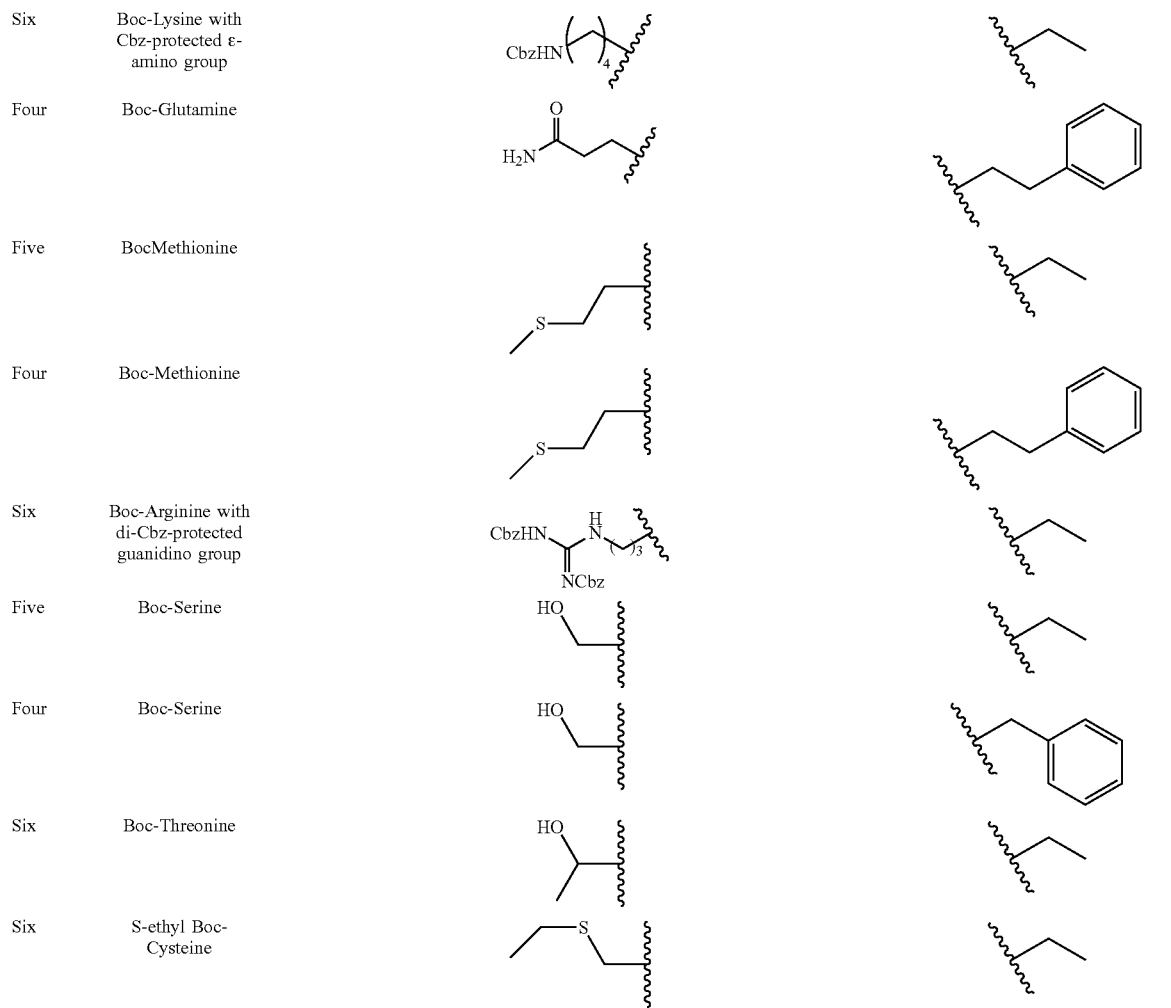
| Method | Amino Compounds | Yield |
| --- | --- | --- |
| Two | Amino compound III-3 | 55% |
| Two | Amino compound III-4 | 37% |
| Two | Amino compound III-5 | 54% |

TABLE 3-continued

Methods, starting materials, R5 and R6 groups, and yields for preparing amino compounds
III-3 to III-5 III-7 to III-16, III-18 to III-20, III-22 to III-23, and III-25 to 111-32.

| Method | Compound | Yield |
|---|---|---|
| Four | Amino compound III-7 | 78% |
| Four | Amino compound III-8 | 78% |
| Two | Amino compound III-9 | 25% |
| Four | Amino compound III-10 | 87% |
| Four | Amino compound III-11 | 90% |
| Four | Amino compound III-12 | 84% |
| Two | Amino compound III-13 | 45% |
| Four | Amino compound III-14 | 76% |

TABLE 3-continued

Methods, starting materials, R5 and R6 groups, and yields for preparing amino compounds
III-3 to III-5 III-7 to III-16, III-18 to III-20, III-22 to III-23, and III-25 to 111-32.

| | | |
|---|---|---|
| Four | Amino compound III-15 | 65% |
| Four | Amino compound III-16 | 81% |
| Five | Amino compound III-18 | 94 % |
| Six | Amino compound III-19 | 63% |
| Six | Amino compound III-20 | 76% |
| Six | Amino compound III-22 | 30% |
| Six | Amino compound III-23 | >99% |

TABLE 3-continued
Methods, starting materials, R5 and R6 groups, and yields for preparing amino compounds
III-3 to III-5 III-7 to III-16, III-18 to III-20, III-22 to III-23, and III-25 to 111-32.
| | | |
|---|---|---|
| Four | 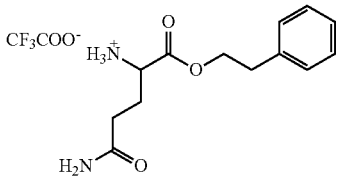  Amino compound III-25 | 35% |
| Five | 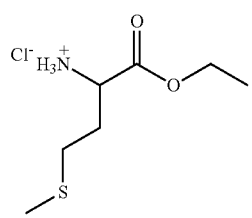  Amino compound III-26 | 91% |
| Four | 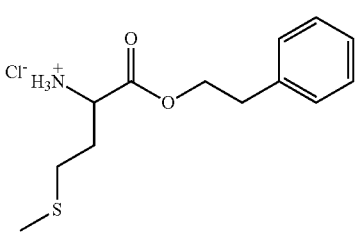  Amino compound III-27 | 73% |
| Six | 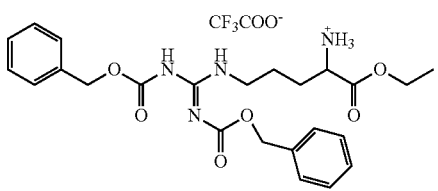  Amino Compound III-28 | >99% |
| Five | 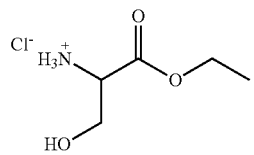  Amino compound III-29 | 95% |
| Four | 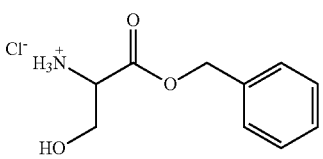  Amino compound III-30 | 89% |
| Six | 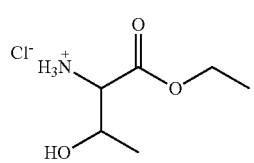  Amino compound III-31 | 64% |

TABLE 3-continued

Methods, starting materials, R5 and R6 groups, and yields for preparing amino compounds
III-3 to III-5 III-7 to III-16, III-18 to III-20, III-22 to III-23, and III-25 to 111-32.

| Six | 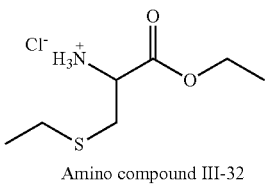 Amino compound III-32 | 21% |
|---|---|---|

TABLE 4

Structural formulas and CAS numbers/designated numbers of various amino compounds, reaction and purification parameters, and structural formulas, designated numbers, appearances, and yields of diazo compounds II-1 to II-34.

| Amino Composition | Equivalents of Reactants (eq) | | |
|---|---|---|---|
| Structural Formulas CAS No./Designated | Amino Compounds | $K_2CO_3$ | N-transfer Reagents |
| 5468-37-1 | 1.2 eq | 4.0 eq | 1.0 Eq |
| Amino compound III-2 | 1.5 eq | 4.0 eq | 1.0 Eq |
| Amino compound III-3 | 1.5 eq | 4.0 eq | 1.0 Eq |
| Amino compound III-4 | 1.5 eq | 4.0 eq | 1.0 Eq |
| Amino compound III-5 | 1.5 eq | 4.0 eq | 1.0 Eq |

TABLE 4-continued

Structural formulas and CAS numbers/designated numbers of various amino compounds, reaction and purification parameters, and structural formulas, designated numbers, appearances, and yields of diazo compounds II-1 to II-34.

| Structure | | | |
|---|---|---|---|
| 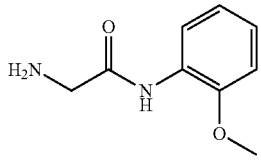<br>Amino compound III-6 | 1.5 eq | 4.0 eq | 1.0 Eq |
| 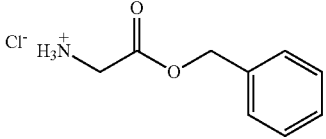<br>Amino compound III-7 | 1.2 eq | 4.0 eq | 1.0 Eq |
| 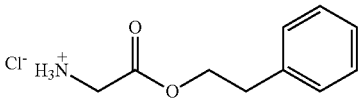<br>Amino compound III-8 | 1.2 eq | 4.0 eq | 1.0 Eq |
| 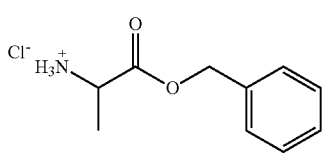<br>Amino compound III-9 | 1.2 eq | 4.0 eq | 1.0 Eq |
| 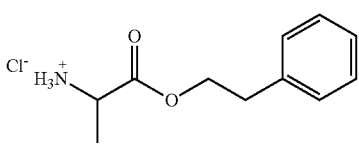<br>Amino compound III-10 | 1.2 eq | 4.0 eq | 1.0 Eq |
| 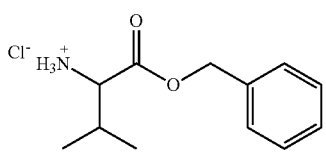<br>Amino compound III-11 | 1.5 eq | 4.0 eq | 1.0 Eq |
| 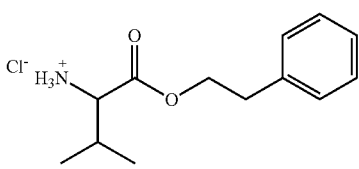<br>Amino compound III-12 | 1.2 eq | 4.0 eq | 1.0 Eq |
| 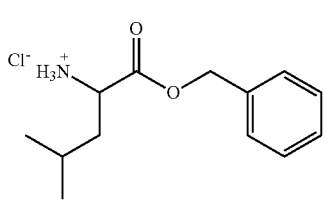<br>Amino compound III-13 | 1.6 eq | 4.0 eq | 1.0 Eq |

TABLE 4-continued

Structural formulas and CAS numbers/designated numbers of various amino compounds, reaction and purification parameters, and structural formulas, designated numbers, appearances, and yields of diazo compounds II-1 to II-34.

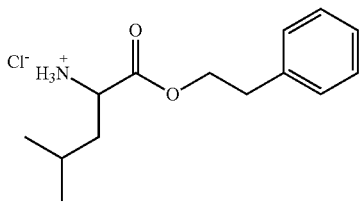

Amino compound III-14

1.2 eq     4.0 eq     1.0 Eq

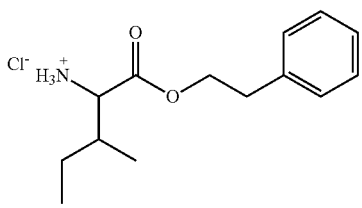

Amino compound III-15

1.2 eq     4.0 eq     1.0 Eq

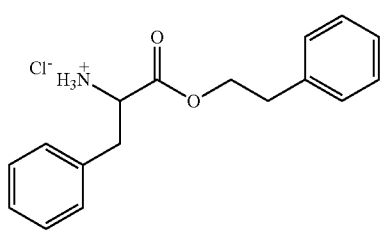

Amino compound III-16

1.2 eq     4.0 eq     1.0 Eq

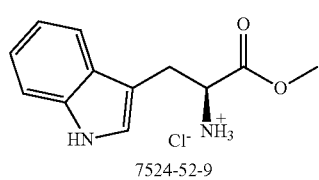 [SMILES: COC(=O)[C@@H](N)Cc1c[nH]c2ccccc12 ; [Cl-]]

7524-52-9

1.2 eq     4.0 eq     1.0 Eq

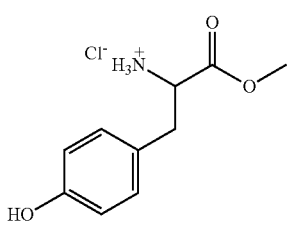

Amino compound III-18

1.2 eq     4.0 eq     1.0 Eq

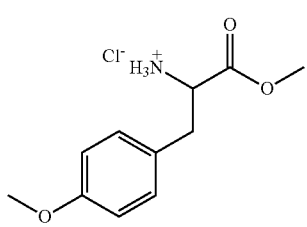

Amino compound III-19

2.0 eq     5.0 eq     1.0 Eq

TABLE 4-continued

Structural formulas and CAS numbers/designated numbers of various amino compounds, reaction and purification parameters, and structural formulas, designated numbers, appearances, and yields of diazo compounds II-1 to II-34.

| | | | |
|---|---|---|---|
| 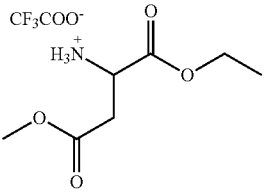<br>Amino compound III-20 | 1.2 eq | 4.0 eq | 1.0 Eq |
| 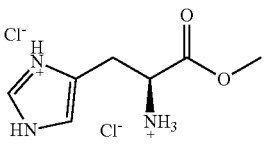<br>Amino compound III-21 | 1.1 eq | 4.0 eq | 1.0 Eq |
| 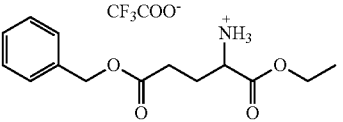<br>Amino compound III-22 | 1.2 eq | 4.0 eq | 1.0 Eq |
| 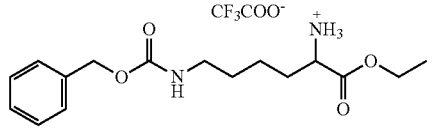<br>Amino compound III-23 | 1.2 eq | 4.0 eq | 1.0 Eq |
| 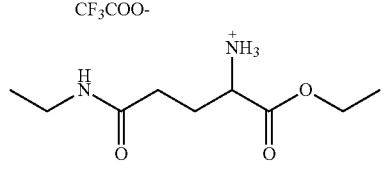<br>Amino compound III-24 | 1.2 eq | 4.0 eq | 1.0 Eq |
| 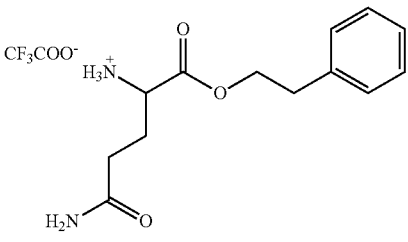<br>Amino compound III-25 | 1.2 eq | 4.0 eq | 1.0 Eq |
| 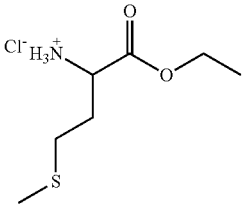<br>Amino compound III-26 | 1.2 eq | 4.0 eq | 1.0 Eq |

TABLE 4-continued

Structural formulas and CAS numbers/designated numbers of various amino compounds, reaction and purification parameters, and structural formulas, designated numbers, appearances, and yields of diazo compounds II-1 to II-34.

| Structure | | | |
|---|---|---|---|
| Amino compound III-27 | 1.2 eq | 4.0 eq | 1.0 Eq |
| Amino compound III-28 | 1.2 eq | 4.0 eq | 1.0 Eq |
| Amino compound III-29 | 1.5 eq | 4.0 eq | 1.0 eq |
| Amino compound III-30 | 1.0 eq | 4.0 eq | 1.0 Eq |
| Amino compound III-31 | 1.2 eq | 4.0 eq | 1.0 Eq |
| Amino compound III-32 | 1.0 eq | 8.2 eq | 2.05 Eq |
| Amino compound III-33 | 2.0 eq. | 5.0 eq | 1.0 Eq |

TABLE 4-continued

Structural formulas and CAS numbers/designated numbers of various amino compounds, reaction and purification parameters, and structural formulas, designated numbers, appearances, and yields of diazo compounds II-1 to II-34.

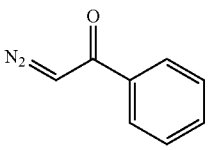

70858-88-7

| | 1.2 eq | 4.0 eq | 1.0 Eq |

| | Diazo Compounds | | |
| --- | --- | --- | --- |
| Eluents Composition | Structural Formulas Designated No. | Appearance | Yield |
| EA/Hex = 3:17 v/v | 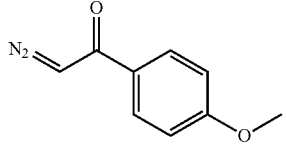<br>Diazo compound II-1 | yellow liquid | 66% |
| EA/Hex = 3:17 v/v | 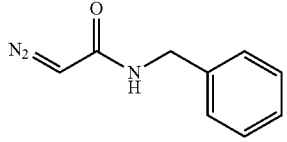<br>Diazo compound II-2 | yellow solid | 79% |
| EA/Hex = 7:13 v/v | 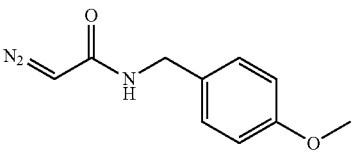<br>Diazo compound II-3 | yellow solid | 86% (NMR) |
| EA/Hex = 2:3 v/v | 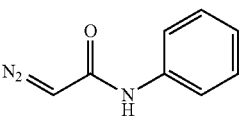<br>Diazo compound II-4 | yellow liquid | 84% (NMR) |
| EA/Hex = 7:13 v/v | 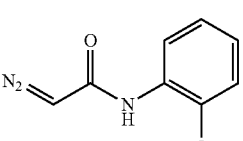<br>Diazo compound II-5 | yellow solid | 85% (NMR) |
| EA/Hex = 7:13 v/v | Diazo compound II-6 | yellow solid | 68% |

TABLE 4-continued

Structural formulas and CAS numbers/designated numbers of various amino compounds, reaction and purification parameters, and structural formulas, designated numbers, appearances, and yields of diazo compounds II-1 to II-34.

| | | | |
|---|---|---|---|
| EA/Hex = 1:3 v/v | 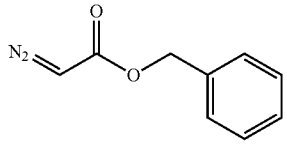\n\nDiazo compound II-7 | yellow solid | 71% |
| DCM/Hex = 3:2 v/v | 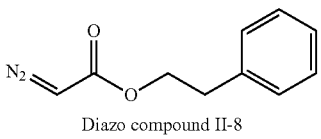\n\nDiazo compound II-8 | yellow solid | 78% |
| EA/Hex = 3:17 v/v | 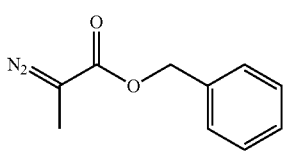\n\nDiazo compound II-9 | yellow oil | 55% (NMR) |
| DCM/Hex = 1:1 v/v | 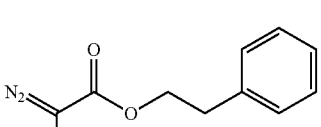\n\nDiazo compound II-10 | yellow oil | 68% |
| EA/Hex = 1:19 v/v | 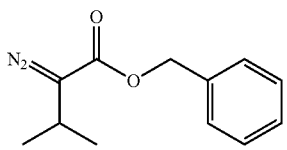\n\nDiazo compound II-11 | yellow oil | 52% |
| DCM/Hex = 1:1 v/v | 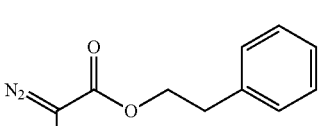\n\nDiazo compound II-12 | yellow oil | 53% |
| EA/Hex = 1:99 v/v | 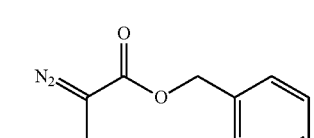\n\nDiazo compound II-13 | yellow oil | 74% |
| EA/Hex = 1:19 v/v | 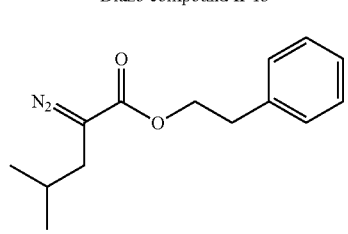\n\nDiazo compound II-14 | yellow oil | 47% |

TABLE 4-continued

Structural formulas and CAS numbers/designated numbers of various amino compounds, reaction and purification parameters, and structural formulas, designated numbers, appearances, and yields of diazo compounds II-1 to II-34.

EA/Hex = 1:19 v/v

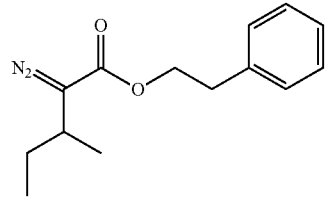

Diazo compound II-15 yellow oil  52%

EA/Hex = 1:7 v/v

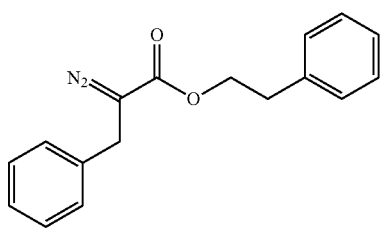

Diazo compound II-16 yellow oil  67%

EA/Hex = 1:14 v/v

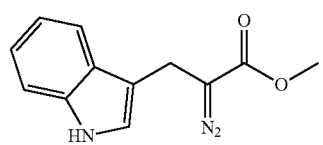

Diazo compound II-17 yellow oil  74%

EA/Hex = 3:17 v/v

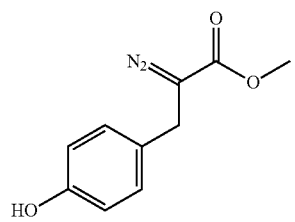

Diazo compound II-18 yellow oil  38%

EA/Hex = 2:3 v/v

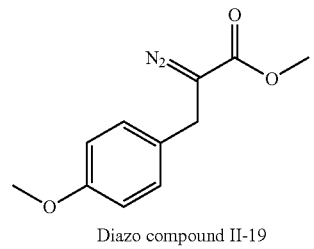

Diazo compound II-19 yellow oil  68%

EA/Hex = 3:17 v/v

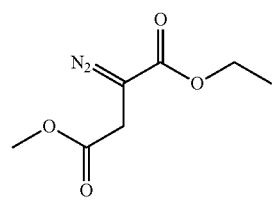

Diazo compound II-20 yellow oil  63%

TABLE 4-continued

Structural formulas and CAS numbers/designated numbers of various amino compounds, reaction and purification parameters, and structural formulas, designated numbers, appearances, and yields of diazo compounds II-1 to II-34.

| | | | |
|---|---|---|---|
| MeOH/DCM = 1:19 v/v | Diazo compound II-21 | yellow oil | 57% |
| EA/Hex = 1:9 v/v | Diazo compound II-22 | yellow oil | 86% |
| EA/Hex = 1:4 v/v | Diazo compound II-23 | yellow oil | 72% |
| EA/Hex = 3:7 v/v | Diazo compound II-24 | yellow oil | 54% |
| EA/Hex = 9:11 v/v | Diazo compound II-25 | yellow oil | 37% |
| DCM/Hex = 2:3 v/v | Diazo compound II-26 | yellow oil | 61% |
| EA/Hex = 3:17 v/v | Diazo compound II-27 | yellow oil | 51% |

TABLE 4-continued

Structural formulas and CAS numbers/designated numbers of various amino compounds, reaction and purification parameters, and structural formulas, designated numbers, appearances, and yields of diazo compounds II-1 to II-34.

| Purification | Structure | Appearance | Yield |
|---|---|---|---|
| EA/Hex = 3:7 v/v | Diazo compound II-28 | yellow oil | 68% |
| EA/Hex = 1:3 v/v | Diazo compound II-29 | yellow oil | 71% |
| EA/Hex = 3:7 v/v | Diazo compound II-30 | yellow oil | 32% |
| A/Hex = 3:17 v/v | Diazo compound II-31 | yellow oil | 17% |
| DCM/Hex = 1:1 v/v | Diazo compound II-32 | yellow oil | 64% |
| EA/Hex = 2:3 v/v | Diazo compound II-33 | yellow oil | 63% |
| EA/Hex = 3:7 v/v | Diazo compound II-34 | yellow oil | 34% |

TABLE 5

Characteristics of diazo compounds II-1 to II-34

| Structural Formulas of Diazo Compounds and Designated No. thereof | Characteristics |
|---|---|
| 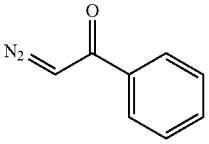<br>Diazo compound II-1 | $^1$H NMR (400 MHz, CDCl$_3$, ppm<br>δ = 7.78-7.75 (m, 2H), 7.58-7.53 (m, 1H), 7.48-7.43(m, 2H), 5.91 (s, 1H);<br>$^{13}$C NMR (100 MHz, CDCl$_3$, ppm)<br>δ = 186.3, 136.7, 132.7, 128.6x2, 126.7x2, 54.1;<br>HRMS (EI$^+$)<br>m/z calculated for C$_8$H$_6$N$_2$O$^+$ 146.0480, found 146.0477. |
| 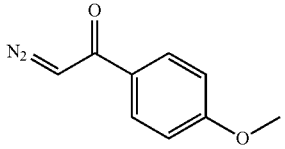<br>Diazo compound II-2 | $^1$H NMR (400 MHz, CDCl$_3$, ppm)<br>δ = 7.73 (m, 2H), 6.92 (m, 2H), 5.84 (s, 1H), 3.85 (s, 3H);<br>$^{13}$C NMR (100 MHz, CDCl$_3$, ppm)<br>δ = 185.3, 163.4, 129.7, 128.9x2, 113.9x2, 55.6, 53.6;<br>HRMS (EI$^+$)<br>m/z calculated for C$_9$H$_8$N$_2$O$_2$$^+$ 176.0578, found 176.0580. |
| 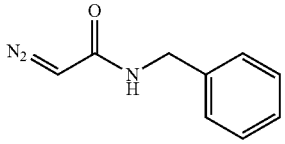<br>Diazo compound II-3 | $^1$H NMR (400 MHz, CDCl$_3$, ppm)<br>δ = 7.36-7.28 (m, 5H), 5.29 (br, 1H), 4.72 (s, 1H), 4.48 (d, J = 5.6 Hz, 2H). |
| 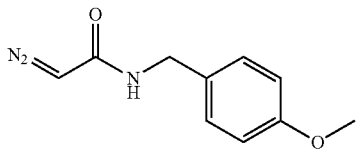<br>Diazo compound II-4 | $^1$H NMR (500 MHz, CDCl$_3$, ppm)<br>δ = 7.21 (ddd, J = 8.6, 2.9, 2.0 Hz, 2H), 6.86 (ddd, J = 8.6, 3.0, 2.2 Hz, 2H), 5.33 (br, 1H), 4.71 (s, 1H), 4.39 (d, J = 5.5 Hz, 2H), 3.79 (s, 3H);<br>$^{13}$C NMR (125 MHz, CDCl$_3$, ppm)<br>δ = 165.4, 159.2, 130.5, 129.3x2, 114.3x2, 55.5, 47.3, 43.7;<br>HRMS (EI$^+$)<br>m/z calculated for C$_{10}$H$_{11}$N$_3$O$_2$$^+$ 205.0849, found 205.0846. |
| 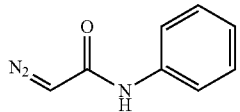<br>Diazo compound II-5 | $^1$H NMR (500 MHz, CDCl$_3$, ppm<br>δ = 7.41 (d, J = 7.5 Hz, 2H), 7.32 (dd, 8.0, 8.0 Hz, 2H), 7.12 (dd, J = 8.0, 8.0 Hz, 1H), 6.78 (br, 1H), 4.89 (s, 1H);<br>$^{13}$C NMR (125 MHz, CDCl$_3$, ppm)<br>δ = 138.0, 129.3x2, 124.7x2, 120.9, 48.6;<br>HRMS (EI$^+$)<br>m/z calculated for C$_8$H$_7$N$_3$O$^+$ 161.0586; found 161.0584. |
| 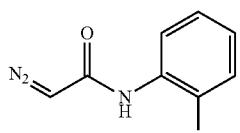<br>Diazo compound II-6 | $^1$H NMR (400 MHz, CDCl$_3$, ppm)<br>δ = 8.28 (d, br, J = 7.6 HZ, 1H), 7.34 (br, 1H), 7.02 (ddd, J = 7.6, 7.6, 1.6 Hz, 6.95 (ddd, J = 7.6, 7.6, 1.6 Hz, 1H), 6.86 (dd, J = 8.0, 1.2 Hz, 1H); 4.96 (s, 1H), 3.86, s, 3H);<br>$^{13}$C NMR (100 MHz, CDCl$_3$, ppm)<br>δ = 163.5, 148.0, 128.1, 123.6, 121.3, 120.1, 110.1, 55.8, 48.9;<br>HRMS (EI$^+$)<br>m/z calculated for C$_9$H$_9$N$_3$O$_2$$^+$ 191.0690, found 191.0689. |
| 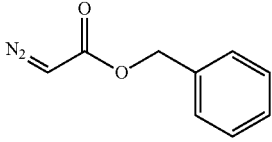<br>Diazo compound II-7 | $^1$H NMR (500 MHz, CDCl$_3$, ppm)<br>δ = 7.38-7.33 (m, 5H), 5.20 (s, 2H), 4.79 (br, 1H);<br>$^{13}$C NMR (125 MHz, CDCl$_3$, ppm)<br>δ = 136.1, 128.8x2, 128.5, 128.4x2, 66.7 46.6;<br>HRMS (EI$^+$)<br>m/z calculated for C$_9$H$_8$N$_2$O$_2$$^+$ 176.0580, found 176.0584. |
| 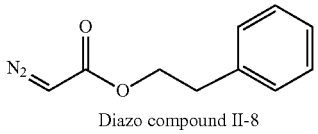<br>Diazo compound II-8 | $^1$H NMR (400 MHz, CDCl$_3$, ppm)<br>δ = 7.33-7.29 (m, 2H), 7.25-7.19 (m, 3H), 4.72 (br, 1H), 4.37 (t, J = 7.2 Hz, 2H), 2.96 (t, J = 7.2 Hz, 2H);<br>$^{13}$C NMR (100 MHz, CDCl$_3$, ppm)<br>δ = 137.8, 129.0x2, 128.6x2, 126.7, 65.4, 46.3, 35.4;<br>HRMS (EI$^+$)<br>m/z calculated for C$_{10}$H$_{10}$N$_2$O$_2$$^+$ 190.0737, found 190.0736. |

TABLE 5-continued

Characteristics of diazo compounds II-1 to II-34

| Structural Formulas of Diazo Compounds and Designated No. thereof | Characteristics |
|---|---|
| 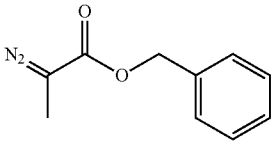<br>Diazo compound II-9 | $^1$H NMR (500 MHz, CDCl$_3$, ppm<br>δ = 7.37-7.32 (m, 5H), 5.21 (s, 2H), 1.98 (s, 3H);<br>13C NMR (125 MHz, CDCl$_3$, ppm)<br>δ = 136.3, 128.7x2, 128.3, 128.2x2, 66.5, 8.61. |
| 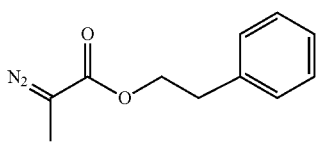<br>Diazo compound II-10 | $^1$H NMR (400 MHz, CDCl$_3$, ppm)<br>δ = 7.33-7.29 (m, 2H), 7.25-7.19 (m, 3H.), 4.36 (t, J = 6 Hz, 2H), 2.95 (t, J = 6.8 Hz, 2H), 1.94 (s, 3H);<br>$^{13}$C NMR (125 MHz, CDCl$_3$, ppm)<br>δ = 138.0, 129.1x2, 128.6x2, 126.7, 65.5, 35.6, 8.5;<br>HRMS (EI$^+$)<br>m/z calculated for C$_{11}$H$_{12}$N$_2$O$_2^+$ 204.0893, found 204.0892. |
| 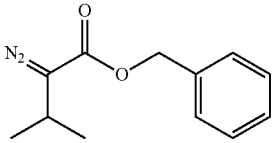<br>Diazo compound II-11 | $^1$H NMR (500 MHz, CDCl$_3$, ppm)<br>δ = 7.39-7.31 (m, 5H), 5.21 (s, 2H), 2.78 (sept, J = 6.9 Hz, 1H), 1.15 (d, J = 6.9 Hz, 6H);<br>$^{13}$C NMR (125 MHz, CDCl$_3$, ppm)<br>δ = 136.4, 128.7x2, 128.3, 128.1x2, 66.3, 23.4, 20.7x2;<br>HRMS (EI$^+$)<br>m/z calculated for C$_{12}$H$_{14}$N$_2$O$_2^+$ 218.1050, found 218.1046. |
| 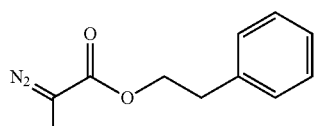<br>Diazo compound II-12 | $^1$H NMR (400 MHZ, CDCl$_3$, ppm)<br>δ = 7.33-7.28 (m, 2H), 7.25-7.20 (m, 3H), 4.36 (t, J = 6.8 Hz, 2H), 2.95 (t, J = 6.8 Hz, 2H), 2.72 (sept, J = 6.9 HZ, 1H), 1.12 (d, J = 6.8 Hz, 6H);<br>$^{13}$C NMR (125 MHz, CDCl$_3$, ppm)<br>δ = 138.0, 129.1x2, 128.6x2, 126.7, 65.2, 35.6, 23.3, 20.6x2;<br>HRMS (EI$^+$)<br>m/z calculated for C$_{13}$H$_{16}$N$_2$O$_2^+$ 232.1206, found 232.1204. |
| 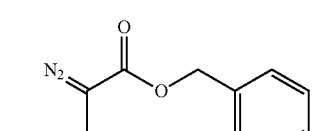<br>Diazo compound II-13 | $^1$H NMR (400 MHz, CDCl$_3$, ppm)<br>δ = 7.39-7.30 (m, 5H), 5.21 (s, 2H), 2.19 (d, J = 6.8 Hz, 2H), 1.83 (nonet, J = 6.8 Hz, 1H), 0.96 (d, J = 6.8 Hz, 6H);<br>$^{13}$C NMR (100 MHz, CDCl$_3$, ppm)<br>δ = 136.4, 128.7x2, 128.3, 128.1x2, 66.4, 32.4, 28.1, 22.0x2;<br>HRMS (EI$^+$)<br>m/z calculated for C$_{13}$H$_{16}$N$_2$O$_2^+$ 232.1206, found 232.1207. |
| 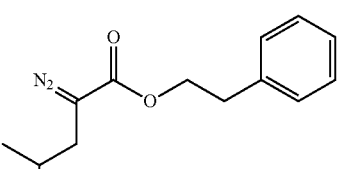<br>Diazo compound II-14 | $^1$H NMR (400 MHz, CDCl$_3$, ppm)<br>δ = 7.32-7.27 (m, 2H), 7.25-7.20 (m, 3H), 4.36 (t, J = 7.0 Hz, 2H), 2.95 (t, J = 7.0 Hz, 2H), 2.13 (d, J = 7.1 Hz, 2H), 1.83 (nonet, J = 6.8 Hz, 1H), 0.93 (d, J = 6.7 Hz, 6H);<br>13C NMR (100 MHz, CDCl$_3$, ppm)<br>δ = 138.0, 129.1x2, 128.6x2, 126.7, 65.3, 35.6, 32.3, 28.1, 22.0x2;<br>HRMS (EI$^+$)<br>m/z calculated for C$_{14}$H$_{18}$N$_2$O$_2^+$ 246.1363, found 246.1360. |
| 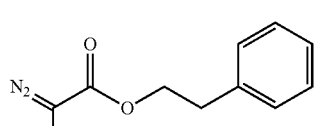<br>Diazo compound II-15 | $^1$H NMR (400 MHz, CDCl$_3$, ppm)<br>δ = 7.32-7.28 (m, 2H), 7.25-7.20 (m, 3H), 4.36 (t, J = 7.0 Hz, 2H), 2.95 (t, J = 7.0 Hz, 2H), 2.47 (sext, J = 7.0 Hz, 1H), 1.49-1.38 (m, 2H), 1.11 (d, J = 7.0 Hz, 3H), 0.91 (t, J = 7.4 Hz, 3H);<br>$^{13}$C NMR (125 MHz, CDCl$_3$, ppm)<br>δ = 138.0, 129.1x2, 128.6x2, 126.7, 65.2, 35.6, 30.0, 27.9, 18.2, 11.7;<br>HRMS (EI$^+$)<br>m/z calculated for C$_{14}$H$_{18}$N$_2$O$_2^+$ 246.1363, found 246.1360. |

TABLE 5-continued

Characteristics of diazo compounds II-1 to II-34

| Structural Formulas of Diazo Compounds and Designated No. thereof | Characteristics |
|---|---|
| (Diazo compound, structure shown) | $^1$H NMR (400 MHz, CDCl$_3$, ppm)<br>δ = 7.33-7.27 (m, 3H), 7.25-7.20 (m, 7H), 4.39 (t, J = 6.9 Hz, 2H), 3.60 (s, 2H), 2.95 (t, J = 6.9 Hz, 2H);<br>$^{13}$C NMR (100 MHz, CDCl$_3$, ppm)<br>δ = 137.9, 137.3, 129.1×2, 128.9×2, 128.6×2, 128.4×2, 127.2, 126.7, 65.5, 35.5, 29.4;<br>HRMS (EI$^+$)<br>m/z calculated for C$_{17}$H$_{16}$N$_2$O$_2$$^+$ 280.1206, found 280.1203. |
| Diazo compound II-17 | $^1$H NMR (500 MHz, CDCl$_3$, ppm)<br>δ = 8.07 (br, 1H), 7.60 (d, J = 7.9 Hz, 1H), 7.37 (ddd, J = 8.1, 0.8, 0.8 Hz, 1H), 7.22 (ddd, J = 8.1, 7.1, 1.1 Hz, 1H), 7.14 (ddd, J = 8.0, 7.1, 1.1 Hz, 1H), 7.09 (d, J = 2.4 Hz, 1H), 3.81 (d, J = 0.9 Hz, 2H), 3.80 (s, 3H);<br>$^{13}$C NMR (125 MHz, CDCl$_3$, ppm)<br>δ = 136.6, 127.0, 122.7, 122.6, 120.0, 119.0, 111.4, 111.4, 52.1, 19.7;<br>HMRS (EI$^+$)<br>m/z calculated for C$_{12}$H$_{11}$N$_3$O$_2$$^+$ 229.0848, found 229.0846. |
| Diazo compound II-18 | $^1$H NMR (500 MHz, CDCl$_3$, ppm)<br>δ = 7.10 (d, J = 8.5 Hz, 2H), 6.78 (d, J = 8.5 Hz, 2H), 5.29 (br, 1H), 3.79 (s, 3H), 3.56 (s, 2H);<br>$^{13}$C NMR (125 MHz, CDCl$_3$, ppm)<br>δ = 155.0; 129.8×2, 129.2, 115.8×2, 52.2, 28.7;<br>HRMS (EI$^+$)<br>m/z calculated for C$_{10}$H$_{10}$N$_2$O$_3$$^+$ 206.0687, found 206.0686, |
| Diazo compound II-19 | $^1$H NMR (400 MHz, CDCl$_3$, ppm)<br>δ = 7.18-7.14 (m, 2H), 6.87-6.84 (m, 2H), 3.79 (s, 3H), 3.78 s, 3H), 3.58 (s, 2H). |
| Diazo compound II-20 | $^1$H NMR (400 MHz, CDCl$_3$, ppm)<br>δ = 4.23 (q, J = 7.1 Hz, 2H), 3.74 (s, 3H), 3.32 (s, 2H), 1.27 (t, J = 7.1 Hz, 3H);<br>$^{13}$C NMR (100 MHz, CDCl$_3$, ppm)<br>δ = 170.2; 166.8, 61.3, 52.6, 28.8, 14.6;<br>HRMS (EI$^+$)<br>m/z calculated for C$_7$H$_{10}$N$_2$O$_4$ [M + Na]$^+$ = 209.0533, found 209.0532. |
| Diazo compound II-21 | $^1$H NMR (500 MHz, CDCl$_3$, ppm)<br>δ = 7.59 (s, 1H), 6.89 (s, 1H), 6.54 (br, 1H), 3.76 (s, 3H), 3.62 (s, 2H);<br>$^{13}$C NMR (125 MHz, CDCl$_3$, ppm)<br>δ = 168.2, 135.4, 133.7, 117.2, 52.2, 21.7;<br>HRMS (EI$^+$)<br>m/z calculated for C$_7$H$_8$N$_4$O$_2$$^+$ 180.0642, found 180.0642. |
| Diazo compound II-22 | $^1$H NMR (400 MHz, CDCl$_3$, ppm)<br>δ = 7.36-7.30 (m, 5H), 5.13 (s, 2H), 4.19 (q, J = 7.1 Hz, 2H), 2.65-2.58 (m, 4H), 1.25 (t, J = 7.1 Hz, 3H);<br>$^{13}$C NMR (100 MHz, CDCl$_3$, ppm)<br>δ = 172.4, 135.8, 128.7×2, 128.5×2, 128.5, 66.7, 60.9, 32.6, 19.7, 14.6;<br>HRMS (EI$^+$)<br>m/z calculated for C$_{14}$H$_{16}$N$_2$O$_4$$^+$ 276.1105, found 276.1106. |

TABLE 5-continued

Characteristics of diazo compounds II-1 to II-34

Structural Formulas of Diazo Compounds and Designated No. thereof | Characteristics
---|---
Diazo compound II-23 | ¹H NMR (400 MHz, CDCl₃, ppm)<br>δ = 7.39-7.30 (m, 5H), 5.09 (s, 2H), 4.77 (br, 1H), 4.21 (q, J = 7.1 Hz, 2H), 3.25-3.20 (m, 2H), 2.34-2.31 (m, 2H), 1.61-1.48 (m, 4H), 1.26 (t, J = 7.1 Hz, 3H);<br>¹³C NMR (100 MHz, CDCl₃, ppm)<br>δ = 167.6, 156.5, 136.6, 128.5x2, 128.1x3, 66.7, 60.8, 40.7, 29.2, 25.0, 22.9, 14.6,<br>HRMS (ESI⁺)<br>m/z calculated for C₁₆H₂₁N₃O₄ [M + Na]⁺ = 342.1424, found 342.1418.
Diazo compound II-24 | ¹H NMR (400 MHz, CDCl₃, ppm)<br>δ = 5.52 (br, 1H), 4.21 (q, J = 7.1 Hz, 2H), 3.29 (qd, J = 7.3, 5.6 Hz, 2H), 2.63 (t, J = 6.6 Hz, 2H), 2.42 (t, J = 6.8 Hz, 2H), 1.27 (t, J = 7.1 Hz, 3H), 1.13 (t, J = 7.2 Hz 3H);<br>¹³C NMR (125 MHz, CDCl₃, ppm)<br>δ = 171.1, 167.6, 60.7, 34.4, 34.2, 19.9, 14.7, 14.5;<br>HRMS (ESI⁺)<br>m/z calculated for C₉H₁₅N₃O₃ [M + Na]⁺ = 236.1006, found 236.1004.
Diazo compound II-25 | ¹H NMR (400 MHz, CDCl₃, ppm)<br>δ = 7.33-7.29 (m, 2H), 7.26-7.20 (m, 3H), 5.35 (br, 2H), 4.37 (t, J = 6.9 Hz, 2H), 2.95 (t, J = 6.9 Hz, 2H), 2.60 (t, J = 6.6 Hz, 2H), 2.43 (br, 2H);<br>¹³C NMR (125 MHz, CDCl₃, ppm)<br>δ = 173.7, 167.6, 137.9, 129.1x2, 128.6x2, 126.7, 65.3, 35.5, 33.5, 19.8;<br>HRMS (ESI⁺)<br>m/z calculated for C₁₃H₁₅N₃O₃ [M + Na]⁺ = 284.1011, found 284.1017.
Diazo compound II-26 | ¹H NMR (400 MHz, CDCl₃, ppm)<br>δ = 4.22 (q, J = 7.2 Hz, 2H), 2.69 (m, 2H), 2.58 (m 2H), 2.13 (s, 3H), 1.27 (t, J = 7.2 Hz, 3H).
Diazo compound II-27 | ¹H NMR (400 MHz, CDCl₃, ppm)<br>δ = 7.33-7.28 (m, 2H), 7.25-7.19 (m, 3H), 4.37 (t, J = 6.9 Hz, 2H), 2.96 (t, J = 6.9 Hz, 2H), 2.70-2.60 (m, 2H), 2.60-2.54 (m, 2H), 2.11 (s, 3H);<br>¹³C NMR (125 MHz, CDCl₃, ppm)<br>δ = 167.2, 137.9, 129.1x2, 128.6x2, 126.7, 65.5, 35.5, 33.0, 24.0, 15.5;<br>HRMS (EI⁺)<br>m/z calculated for C₁₃H₁₆N₂O₂S⁺ 264.0927, found 264.0927,
Diazo compound II-28 | ¹H NMR (400 MHz, CDCl₃, ppm)<br>δ = 9.44 (br, 1H), 9.25 (br, 1H), 7.41-7.28 (m, 10H), 5.25 (s, 2H), 5.14 (s, 2H), 4.17 (q, J = 7.1, 2H), 4.04 (dd, J = 7.4, 7.4 Hz, 2H), 2.30 (t, J = 7.5 Hz, 2H), 1.81 (m, 2H), 1.23 (t, J = 7.1 Hz, 3H);<br>¹³C NMR (125 MHz, CDCl₃, ppm)<br>δ = 167.4, 164.0, 160.5, 155.9, 137.0, 134.7, 128.91, 128.88x2, 128.5x2, 128.4x2, 128.0x2, 127.9, 69.1, 67.1, 6.8, 43.9, 26.8, 20.6, 14.6;<br>HRMS (ESI⁺)<br>m/z calculated for C₂₄H₂₇N₅O₆ [M + Na]⁺ = 504.1859, found 504.1852.

TABLE 5-continued

Characteristics of diazo compounds II-1 to II-34

| Structural Formulas of Diazo Compounds and Designated No. thereof | Characteristics |
|---|---|
| 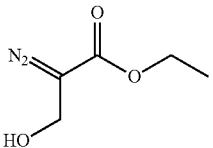<br>Diazo compound II-29 | $^1$H NMR (500 MHZ, CDCl$_3$, ppm)<br>δ = 4.50 (s, 2H), 4.25 (q, J = 7.0, 2H), 1.29 (t, J = 7.0, 3H);<br>$^{13}$C NMR (125 MHz, CDCl$_3$, ppm)<br>δ = 166.7, 61.3, 57.9, 14.6;<br>HRMS (EI$^+$)<br>m/z calculated for C$_5$H$_8$N$_2$O$_3$$^+$ 144.0529, found 144.0530. |
| 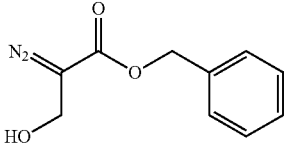<br>Diazo compound II-30 | $^1$H NMR (500 MHz, CDCl$_3$, ppm)<br>δ = 7.37-7.33 (m, 5H), 5.23 (s, 2H), 4.52 (s, 2H);<br>$^{13}$C NMR (125 MHz, CDCl$_3$, ppm)<br>δ = 166.4, 135.9, 128.8x2, 128.5, 128.3x2, 66.8, 58.0;<br>HRMS (EI$^+$)<br>m/z calculated for C$_{10}$H$_{10}$N$_2$O$_3$$^+$ 206.0686, found 206.0685. |
| 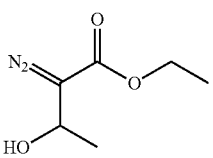<br>Diazo compound II-31 | $^1$H NMR (400 MHz, CDCl$_3$, ppm)<br>δ = 4.93 (q, J = 6.6 Hz, 1H), 4.25 (q, J = 7.1 Hz, 2H), 1.41 (d, J = 6.6 Hz, 3H), 1.29 (t, J = 7.1 Hz, 3H);<br>$^{13}$C NMR (100 MHz, CDCl$_3$, ppm)<br>δ = 166.7, 62.7, 61.2, 31.1, 19.7, 14.6;<br>HRMS (ESI$^+$)<br>m/z calculated for C$_6$H$_{10}$N$_2$O$_3$ [M + Na]$^+$ = 181.0584, found 181.0581. |
| 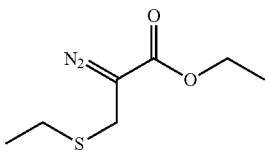<br>Diazo compound II-32 | $^1$H NMR (400 MHz, CDCl$_3$, ppm)<br>δ = 4.24 (q, J = 7.1 Hz, 2H), 3.53 (s, 2H), 2.60 (q, J = 7.4 Hz, 2H), 1.26 (t, J = 7.2 Hz, 3H), 1.26 (t, J = 7.2 Hz, 3H);<br>$^{13}$C NMR (125 MHz, CDCl$_3$, ppm)<br>δ = 166.6, 61.2, 26.1, 25.8 14.7, 14.6;<br>HRMS (EI$^+$)<br>m/z calculated for C$_7$H$_{12}$N$_2$O$_2$S$^+$ 188.0614, found 188.0610. |
| 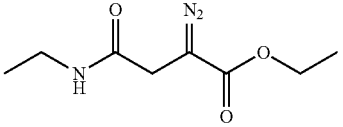<br>Diazo compound II-33 | $^1$H NMR (400 MHz, CDCl$_3$, ppm)<br>δ = 5.95 (br, 1H), 4.25 (q, J = 7.1 Hz, 2H), 3.29 (qd, J = 7.3, 5.6 Hz, 2H), 3.10 (s, 2H), 1.29 (t, J = 7.1 Hz, 3H), 1.14 (t, J = 7.3 Hz, 2H);<br>$^{13}$C NMR (100 MHz, CDCl$_3$, ppm)<br>δ = 169.0, 167.6, 61.4, 34.8, 30.9, 14.8, 14.6;<br>HRMS (ESI$^+$)<br>m/z calculated for C$_8$H$_{13}$N$_3$O$_3$ [M + Na]$^+$ = 222.0849, found 222.0846. |
| 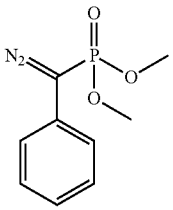<br>Diazo compound II-34 | $^1$H NMR (500 MHz, CDCl$_3$, ppm)<br>δ = 7.40-7.36 (m, 2H), 7.17-7.14 (m, 3H), 3.83 (d, J = 12.0 Hz, 6H);<br>HRMS (EI$^+$)<br>m/z calculated for C$_9$H$_{11}$N$_2$O$_3$P$^+$ 226.0502, found 226.0503. |

TABLE 6

Reaction parameters, times and yields for converting amino compound III-3 to diazo compound II-3 by using N-transfer reagents I-1 to I-7 and I-11.

| N-transfer Reagents | | Equivalents of Reactants | | |
|---|---|---|---|---|
| Structural Formulas Designated No. | Equiv. | $H_3\overset{+}{N}\underset{CF_3COO^-}{\diagdown}\overset{O}{\underset{}{\diagup}}\underset{H}{N}\diagdown\text{Bn}$ | Amino Compound III-3 | $K_2CO_3$ |
| N-transfer reagent I-1 (4-F-phenyl ester, $N_2^+ PF_6^-$) | 1.0 eq | 1.5 eq | 1.0 eq | 4.0 eq |
| N-transfer reagent I-2 (4-Cl-phenyl ester, $N_2^+ PF_6^-$) | | | 1.0 eq | |
| N-transfer reagent I-3 (4-acetyl-phenyl ester, $N_2^+ PF_6^-$) | | | 1.0 eq | |
| N-transfer reagent I-4 (4-methoxy-phenyl ester, $N_2^+ PF_6^-$) | | | 1.0 eq | |
| N-transfer reagent I-5 (2,4,6-trimethyl-phenyl ester, $N_2^+ PF_6^-$) | | | 1.0 eq | |

TABLE 6-continued

| Structure | Equivalents |
|---|---|
| N-transfer reagent I-6 (2-diazonium phenyl propanoate 4-methylphenyl ester, PF$_6^-$) | 1.0 eq |
| N-transfer reagent I-7 (2-diazonium phenyl propanoate phenyl ester, PF$_6^-$) | 1.0 eq |
| N-transfer reagent I-11 (5-methoxy-2-diazonium phenyl propanoate 4-fluorophenyl ester, PF$_6^-$) | 1.5 eq |

| Reaction Time (hour) | Diazo Compound Structural Formula Designated No. | Yield |
|---|---|---|
| 3 | Diazo compound II-3 (N$_2$–CH$_2$–C(=O)–NH–CH$_2$–C$_6$H$_5$) | 77% |
| 4 | | 86% |
| 16 | | 71% |
| 1 | | 63% |
| 16 | | 52% |
| 16 | | 12% |
| 16 | | 48% |
| 13 | | 40% |
| 20 | | 85% |

Test Example 1: Storage Stability Test of N-Transfer Reagents

In this test example, the N-transfer reagents I-1, I-8, I-11, and I-12 were used as test samples. For ease of explanation, the N-transfer reagent I-1 is used as an example to illustrate how this test was performed. It is noted that the other N-transfer reagents I-8, I-11, and I-12 were tested in the same way.

A part of just-synthesized N-transfer reagent I-1 was dissolved in a deuterated solvent to form a solution. Next, a dropper was used to absorb an appropriate amount of the solution and then transferred it to an NMR tube. The rest of the just-synthesized N-transfer reagent I-1 was put into two sample bottles, which were then filled with nitrogen gas. One of the sample bottles was stored at room temperature, and the other was stored at 0° C.

The NMR tube was put in a Bruker Avance III-400 MHz NMR spectrometer to generate a $^1$H NMR spectrum at room temperature, and the spectrum was labeled "Day 0". On the next day at the same time, an appropriate amount of the N-transfer reagent I-1 was taken from the two sample bottles and used to generate $^1$H NMR spectra likewise. The two obtained spectra were labeled "Day 1, room temperature" and "Day 1, 0° C.," respectively. For the N-transfer reagent I-1 in any of the two sample bottles, the $^1$H NMR spectrum thereof was generated day after day until changes in a $^1$H NMR spectrum were found, and the number of the day labelled in the last unchanging spectrum was the duration of stability of the N-transfer reagent I-1 under a specific storage environment. The storage life of the N-transfer reagents I-1, I-8, I-11, and I-12 are listed in Table 7 below.

TABLE 7

Results of storage stability test of N-transfer reagents I-1, I-8, I-11, and I-12.

| N-transfer Reagents | Deuterated Solvent | Storage Life (days) Room Temperature | 0° C. |
|---|---|---|---|
| N-transfer reagent I-1 | CD₃OD | 3 | 44 |
| N-transfer reagent I-8 | CD₃OD | At least 6 months | At least 6 months |
| N-transfer reagent I-11 | CD₃CN | At least 6 months | At least 6 months |
| N-transfer reagent I-12 | CD₃CN | At least 6 months | At least 6 months |

Test Example 2: Thermogravimetric Analysis of N-Transfer Reagent

The N-transfer reagent I-1 was used as a test sample to conduct a thermogravimetric analysis by using a thermogravimetric analyzer (brand: TA Instrument; model: TA-Q50). In this test example, the N-transfer reagent I-1 was heated and the mass thereof was monitored during nitrogen purging. The temperature at which the mass of the test sample is 5.0% less than the mass measured at the initial temperature was shown in Table 8.

TABLE 8

Decomposition temperature of N-transfer reagent I-1 in the thermogravimetric analysis.

| N-transfer Reagent Structural Formula | Designated No. | Decomposition Temperature |
|---|---|---|
| | N-transfer Reagent I-1 | 75° C. |

Test Example 3: Selection of Basic Reagents

In this test example, a triazene intermediate obtained by reacting the N-transfer reagent I-12 with the amino compound II-3 was put into a sample bottle and dissolved in THF (entries 1 to 4) or a mixture of THF and water at the volume ratio of 20:1 (entries 5 to 8) to form a solution, to which a basic reagent was added to form a mixture. The mixture was stirred at room temperature and monitored by TLC. Upon completion, a portion of the mixture was used to generate a $^1$H NMR spectrum, and the conversion ratio from the triazene intermediate to the diazo compound II-3 was calculated via the $^1$H NMR spectrum. Conversion ratios of the triazene intermediate by employing different basic reagents were shown in Table 9 below. Herein, based on the equivalent of the triazene intermediate, the equivalent of the basic reagent is one equivalent, i.e. the equivalent of the basic reagent relative to the equivalent of the triazene intermediate is 1:1. The basic reagents that were tested include triethylamine (Et$_3$N), N,N-diisopropylethylamine (DIPEA), 4-dimethylaminopyridine (DMAP), 1,4-diazabicyclo[2.2.2]octane (DABCO), sodium phosphate (Na$_3$PO$_4$), disodium hydrogen phosphate (Na$_2$HPO$_4$), potassium phosphate (K$_3$PO$_4$), and dipotassium hydrogen phosphate (K$_2$HPO$_4$).

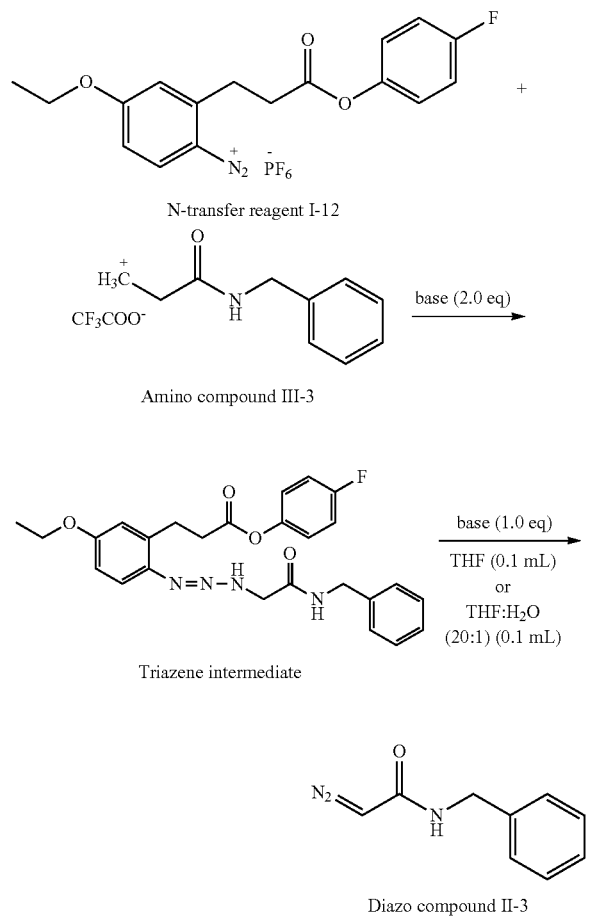

TABLE 9

Ratios of conversion to diazo compound II-3 by reacting triazene intermediate with different basic reagents.

| | Basic Reagents | Reaction Time (hr) | Conversion Ratios from Triazene to Diazo Compound II-3 |
|---|---|---|---|
| 1 | Et$_3$N | 24 | 74% |
| 2 | DIPEA | 24 | 50% |
| 3 | DMAP | 24 | 59% |
| 4 | DABCO | 24 | 92% |
| 5 | Na$_3$PO$_4$ | 24 | 69% |
| 6 | Na$_2$HPO$_4$ | 24 | 8% |
| 7 | K$_3$PO$_4$ | 5.5 | >99% |
| 8 | K$_2$HPO$_4$ | 24 | 3% |

Discussion

By choosing an appropriate nitrobenzene precursor, various novel N-transfer reagents can be synthesized by the method featuring a few steps and simple purification. As can be seen from Table 1, the yields of the N-transfer reagents of the present invention were above 70%, even above 85%, or as high as 94%.

As can be seen from Table 4, by means of using the N-transfer reagents of the present invention, various amino compounds were directly converted into their corresponding diazo compounds under mild alkaline conditions. The N-transfer reagents only reacted with amino groups, while other sensitive functional groups of amino compounds were not reacted or converted into unwanted functional groups. Employing the N-transfer reagents of the present invention to synthesize diazo compounds not only obviates the need for an acid condition required to diazotizing amino compounds but also solves the problem that synthesized diazo compounds are prone to decompose by eliminating nitrogen gas under an acidic condition. Further, inability to undergo diazotization of amino compounds with acid-sensitive functional groups under harsh acidic conditions is also resolved. In addition, the method for synthesizing diazo compounds of the present invention can greatly reduce the number of reaction steps, the cost of production as well as the environmental pollution, and enhance the industrial value of diazo compounds.

As also can be seen from Table 4, diazo compounds II-7 to II-33 were synthesized by reacting different amino acids and their derivatives (α-amino esters) with the N-transfer reagent of the present invention. From the experimental results, it is known that the N-transfer reagent of the present invention can easily convert amino groups of diverse amino acids into diazo groups, succeeding in synthesizing various diazo compounds. In particular, for amino acids that are highly substituted and sterically hindered, they can be easily converted into diazo compounds with high yields by the N-transfer reagent of the present invention. In addition, the N-transfer reagent of the present invention did also convert α-amino ketones and α-amino amides into α-diazo ketones (e.g. diazo compounds II-1 to II-2) and α-diazo amides (e.g. diazo compounds II-3 to II-6) in only one step and with high yields. Further, in addition to the amino compound with a carbonyl group, the N-transfer reagent of the present invention also directly converted an α-amino phosphonate ester into its corresponding diazo compound (e.g. the diazo compound II-34).

As can be seen from Table 6, compared with the N-transfer reagent I-7, the N-transfer reagents I-4 to I-6 contained electron-donating R substitutes, while the N-transfer reagents I-1 to I-3 contained electron-withdrawing R$^1$ substitutes. In comparison with the yield of the diazo compound II-3 by using the N-transfer reagent I-7, the yields of that by using the N-transfer reagents I-4 and I-6 were higher, but the yield of that by using the N-transfer reagent I-5 was lower because of bulky $R^1$ substitutes in the N-transfer reagent I-5. It is also observed that the yields of the diazo compound II-3 were also improved by using the N-transfer reagents I-1 to I-3. In particular, the yield of the diazo compound II-3 by using the N-transfer reagent I-1 was almost doubled, and the yield of that further increased to 86% if the equivalents of the amino compound III-3 increase from 1 to 1.5. In addition, N-transfer reagents with suitable electron-withdrawing $R^1$ substitutes (e.g. the N-transfer reagents I-1 and I-3) could shorten the time of diazotization to 3 hrs or even 1 hr.

As also can be seen from Table 6, using an N-transfer reagent with a $R^2$ substitute (e.g. the N-transfer reagents I-11) could also increase the yield of the diazo compound II-3.

As indicated by Table 6, the R and $R^2$ substituents of the N-transfer reagents could increase the yield of the diazo compound, wherein the electron-withdrawing $R^1$ substitutes could exert a stronger influence on the yield than the electron-donating $R^1$ substitutes. In addition, N-transfer reagents with electron-withdrawing $R^1$ substitutes could also shorten the reaction time.

As can be seen from Table 7, the N-transfer reagent I-1 without any $R^2$ substitute decomposed on the $4^{th}$ day when being stored at room temperature; however, if the storage temperature decreased to 0° C., the N-transfer reagent I-1 did not decompose until the $45^{th}$ day when being stored at 0° C. The N-transfer reagents I-8, I-11, and I-12, each of which contains a $R^2$ substitute, could be stored at room temperature for at least 6 months. It can be known that $R^2$ substitutes can effectively increase the storage stability of the N-transfer reagents.

As can be seen from Table 8, the decomposition temperature of the N-transfer reagent I-1 in the thermogravimetric analysis was 75° C. This means if heating is required during a reaction of a certain amino compound and an N-transfer reagent, the N-transfer reagent I-1 remained stable in a heating condition of 50° C. to 70° C.

As can be seen from Table 9, organic bases such as $Et_3N$, DIPEA, DMAP, and DABCO could effectively convert the triazene intermediate into the diazo compound, the use of DABCO increased the conversion ratio of the triazene intermediate to 92%. In addition, inorganic bases such as $Na_3PO_4$, $Na_2HPO_4$, $K_3PO_4$, and $K_2HPO_4$ could also convert the triazene intermediate to the diazo compound, and the $K_3PO_4$ can convert the triazene intermediate into the diazo compound with a conversion ratio of almost 100%.

In summary, the novel N-transfer reagents of the present invention can directly convert various amino compounds into corresponding diazo compounds under mild conditions, while the other sensitive functional groups of amino compounds remain intact, thereby improving the conversion efficiency of functional groups in chemical reactions.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An N-transfer reagent represented by the following Formula (I):

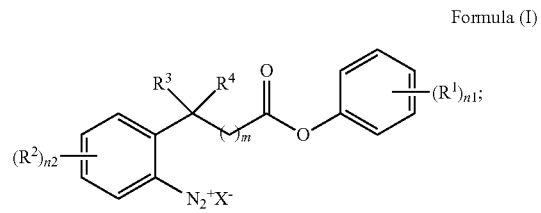

Formula (I)

wherein n1 is an integer from 0 to 5, and $R^1$ is selected from the group consisting of: a deuterium atom, a halogen atom, an alkyl group having 1 to 12 carbon atoms, an alkoxy group having 1 to 12 carbon atoms, an aldehyde group having 1 to 12 carbon atoms, a ketone group having 2 to 12 carbon atoms, an ester group having 2 to 12 carbon atoms, an acyloxy group having 2 to 12 carbon atoms, a sulfonic acid group, a sulfonyl group having 1 to 12 carbon atoms, an amide group having 1 to 12 carbon atoms, and an aryl group having 6 to 18 carbon atoms;

wherein n2 is an integer from 0 to 4, and $R^2$ is selected from the group consisting of: a deuterium atom, a halogen atom, an alkyl group having 1 to 12 carbon atoms, an alkoxy group having 1 to 12 carbon atoms, an aldehyde group having 1 to 12 carbon atoms, a ketone group having 2 to 12 carbon atoms, an ester group having 2 to 12 carbon atoms, an acyloxy group having 2 to 12 carbon atoms, a polyether group having 3 to 12 carbon atoms, a sulfonic acid group, a sulfonyl group having 1 to 12 carbon atoms, an amide group having 1 to 12 carbon atoms, and an aryl group having 6 to 18 carbon atoms; or when n2 is 2, the two $(R^2)$s are adjacent and connect with each other to form a 1,3-dioxolane group or a 1,4-dioxane group;

wherein $R^3$ and $R^4$ are each independently selected from the group consisting of: a hydrogen atom, a deuterium atom, and an alkyl group having 1 to 6 carbon atoms;

wherein $X^-$ is selected from the group consisting of: a hexafluorophosphate anion, a tetrafluoroborate anion, a halogen anion, and a p-toluenesulfonate anion; and wherein m is an integer from 0 to 3.

2. The N-transfer reagent as claimed in claim 1, wherein m is 1.

3. The N-transfer reagent as claimed in claim 1, wherein $R^3$ is the hydrogen atom, and $R^4$ is the hydrogen atom.

4. The N-transfer reagent as claimed in claim 1, wherein $X^-$ is the hexafluorophosphate anion.

5. The N-transfer reagent as claimed in claim 1, wherein n1 is an integer from 1 to 4, and $R^1$ is a fluorine atom, a chlorine atom, a bromine atom, an iodine atom, a methoxy group, or an acetyl group.

6. The N-transfer reagent as claimed in claim 1, wherein n1 is an integer from 1 to 3, and $R^1$ is a methyl group, an ethyl group, a propyl group, or a butyl group.

7. The N-transfer reagent as claimed in claim 1, wherein n2 is an integer from 1 to 3, and each $R^2$ is a fluorine atom, a chlorine atom, a bromine atom, an iodine atom, a methoxy group, an ethoxy group, a methyl ester group, an acetoxy group, an ethylene oxide methyl ether group, a diethylene oxide methyl ether group, or a triethylene oxide ethyl ether group; or n2 is the integer 2, and the two (R²)s are adjacent and connect with each other to form the 1,3-dioxolane group.
8. The N-transfer reagent as claimed in claim 1, wherein the N-transfer reagent is selected from the group consisting of the following:
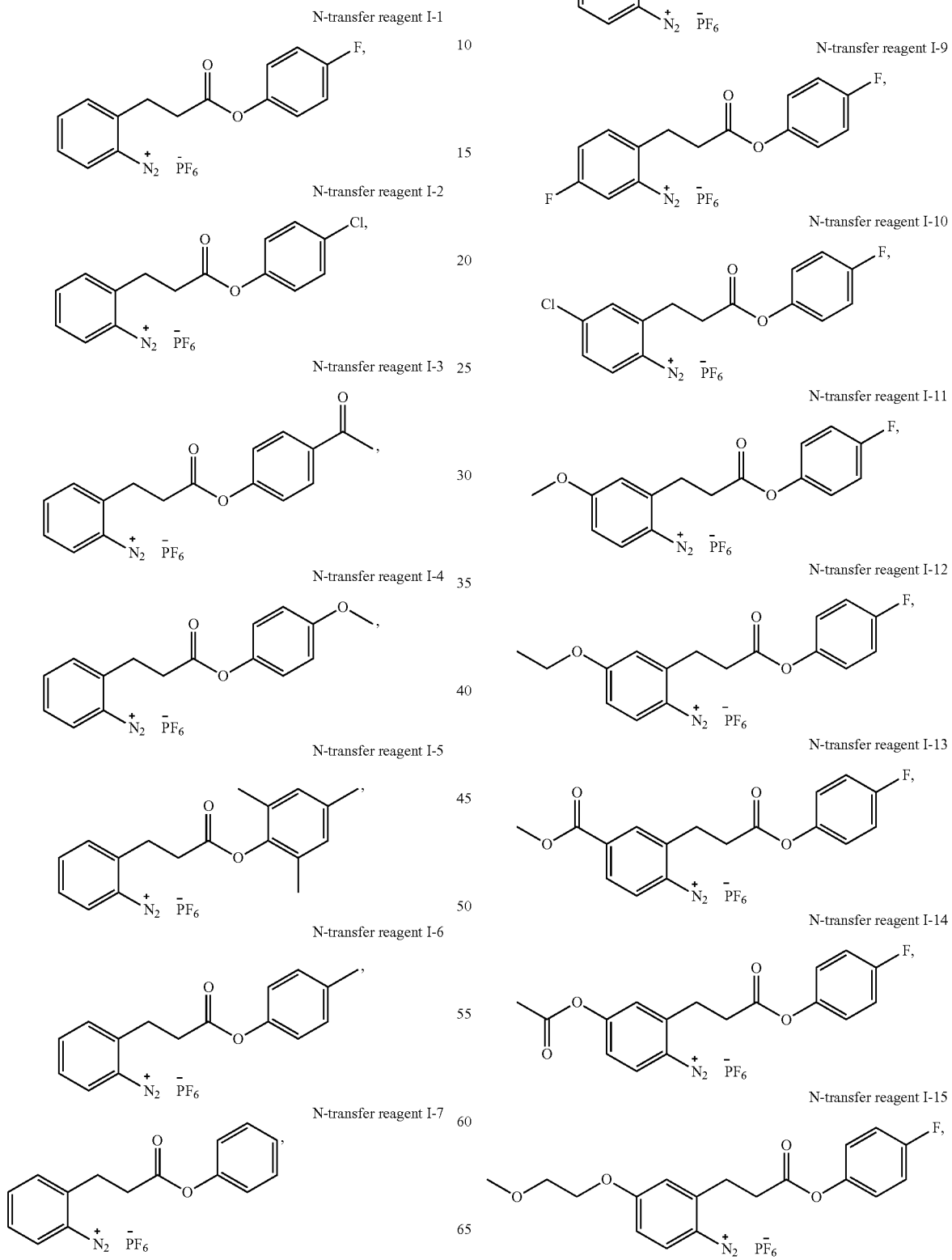

N-transfer reagent I-16

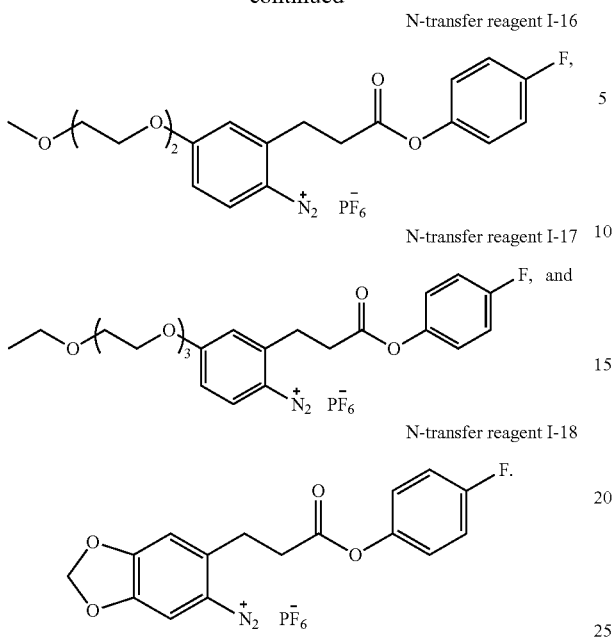

N-transfer reagent I-17

N-transfer reagent I-18

9. A method for producing the N-transfer reagent as claimed in claim 1, comprising the following steps:
step (A): reacting a nitrobenzene precursor represented by the following Formula (II) with a metal catalyst in an atmosphere containing a hydrogen gas to obtain an aniline compound,

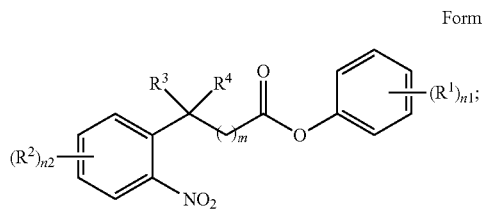

Formula (II)

wherein n1 is an integer from 0 to 5, and $R^1$ is selected from the group consisting of: a deuterium atom, a halogen atom, an alkyl group having 1 to 12 carbon atoms, an alkoxy group having 1 to 12 carbon atoms, an aldehyde group having 1 to 12 carbon atoms, a ketone group having 2 to 12 carbon atoms, an ester group having 2 to 12 carbon atoms, an acyloxy group having 2 to 12 carbon atoms, a sulfonic acid group, a sulfonyl group having 1 to 12 carbon atoms, an amide group having 1 to 12 carbon atoms, and an aryl group having 6 to 18 carbon atoms;
wherein n2 is an integer from 0 to 4, and $R^2$ is selected from the group consisting of: a deuterium atom, a halogen atom, an alkyl group having 1 to 12 carbon atoms, an alkoxy group having 1 to 12 carbon atoms, an aldehyde group having 1 to 12 carbon atoms, a ketone group having 2 to 12 carbon atoms, an ester group having 2 to 12 carbon atoms, an acyloxy group having 2 to 12 carbon atoms, a polyether group having 3 to 12 carbon atoms, a sulfonic acid group, a sulfonyl group having 1 to 12 carbon atoms, an amide group having 1 to 12 carbon atoms, and an aryl group having 6 to 18 carbon atoms; or when n2 is 2, the two $(R^2)$s are adjacent and connect with each other to form a 1,3-dioxolane group or a 1,4-dioxane group;
wherein $R^3$ and $R^4$ are each independently selected from the group consisting of: a hydrogen atom, a deuterium atom, and an alkyl group having 1 to 6 carbon atoms; and
wherein m is an integer from 0 to 3; and
step (B): reacting the aniline compound with a nitrosonium ion to undergo diazotization so as to obtain the N-transfer reagent.

10. The method as claimed in claim 9, wherein the step (B) further comprises:
step (b1): reacting the aniline compound with the nitrosonium ion to undergo diazotization so as to obtain a mixture; and
step (b2): purifying the mixture by concentrating, recrystallizing, or a sedimentation method to obtain the N-transfer reagent.

11. The method as claimed in claim 9, wherein the method is performed at a temperature from −15° C. to 25° C.

12. The method as claimed in claim 9, wherein the amount of the metal catalyst is 5% to 20% of the weight of the nitrobenzene precursor.

13. The method as claimed in claim 9, wherein the metal catalyst comprises palladium on carbon, a platinum metal, a tin metal, a rubidium metal, a rhodium metal, a ruthenium metal, or an iridium metal.

14. An application of the N-transfer reagent as claimed in claim 1, wherein the application comprises: reacting an amino compound and the N-transfer reagent as claimed in claim 1 with a basic reagent in a solvent to convert the amino compound into a diazo compound.

15. The application as claimed in claim 14, wherein the application is performed at a temperature from −10° C. to 50° C.

16. The application as claimed in claim 14, wherein the basic reagent comprises potassium carbonate, potassium bicarbonate, sodium carbonate, sodium bicarbonate, sodium phosphate, sodium hydrogen phosphate, potassium phosphate, potassium hydrogen phosphate, triethylamine, N,N-diisopropylethylamine, 4-dimethylaminopyridine, 1,4-diazabicyclo[2.2.2]octane, or 1,8-diazabicyclo[5.4.0]undec-7-ene.

17. The application as claimed in claim 14, wherein the amino compound comprises an α-amino ketone, an α-amino amide, an α-amino ester, or an α-amino phosphonate ester.

18. The application as claimed in claim 14, wherein the diazo compound is selected from the group consisting of the following:

Diazo compound II-1

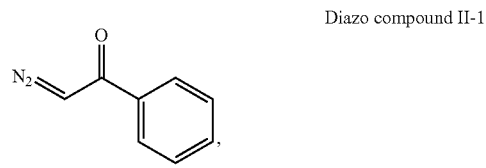

Diazo compound II-2

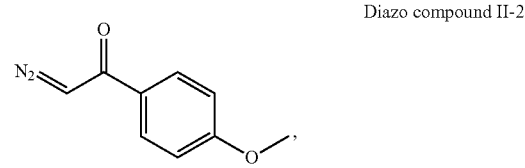

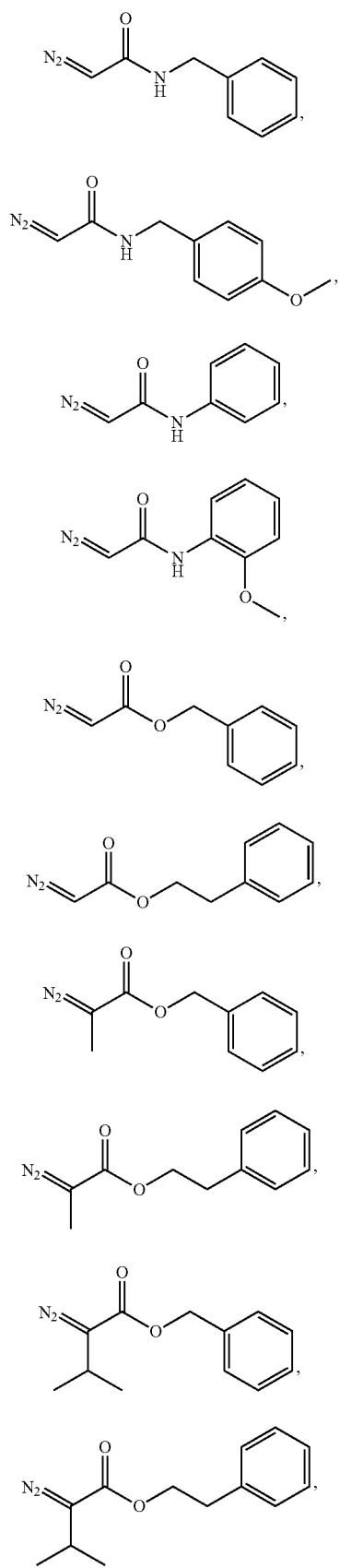
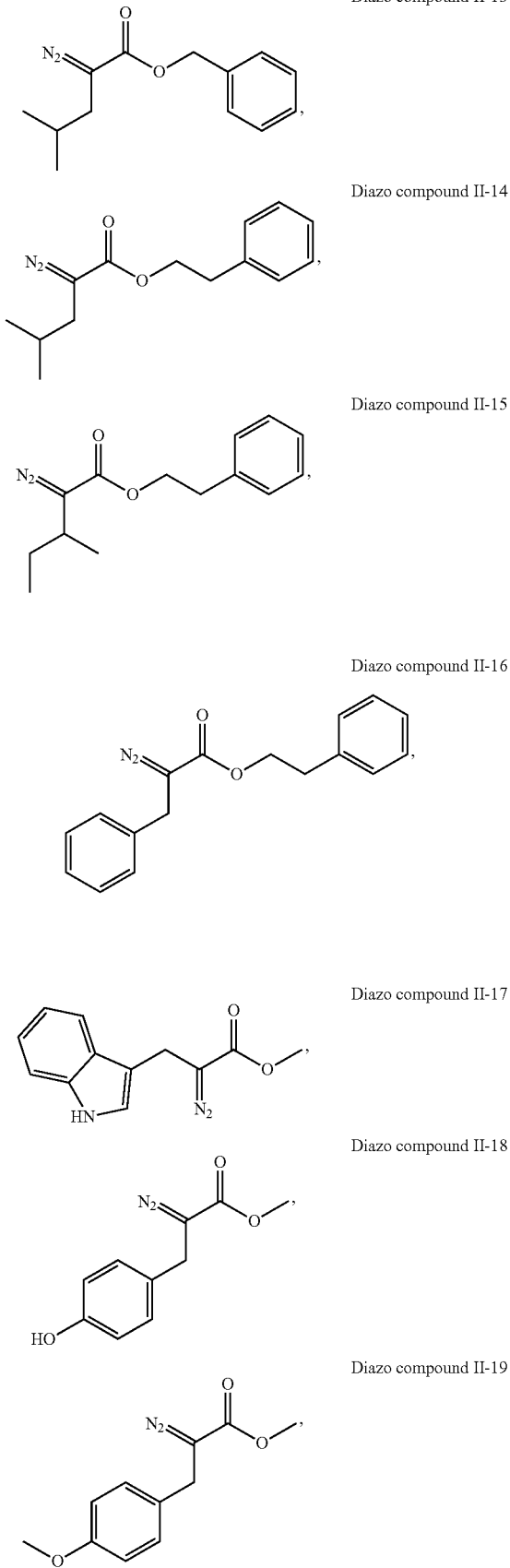

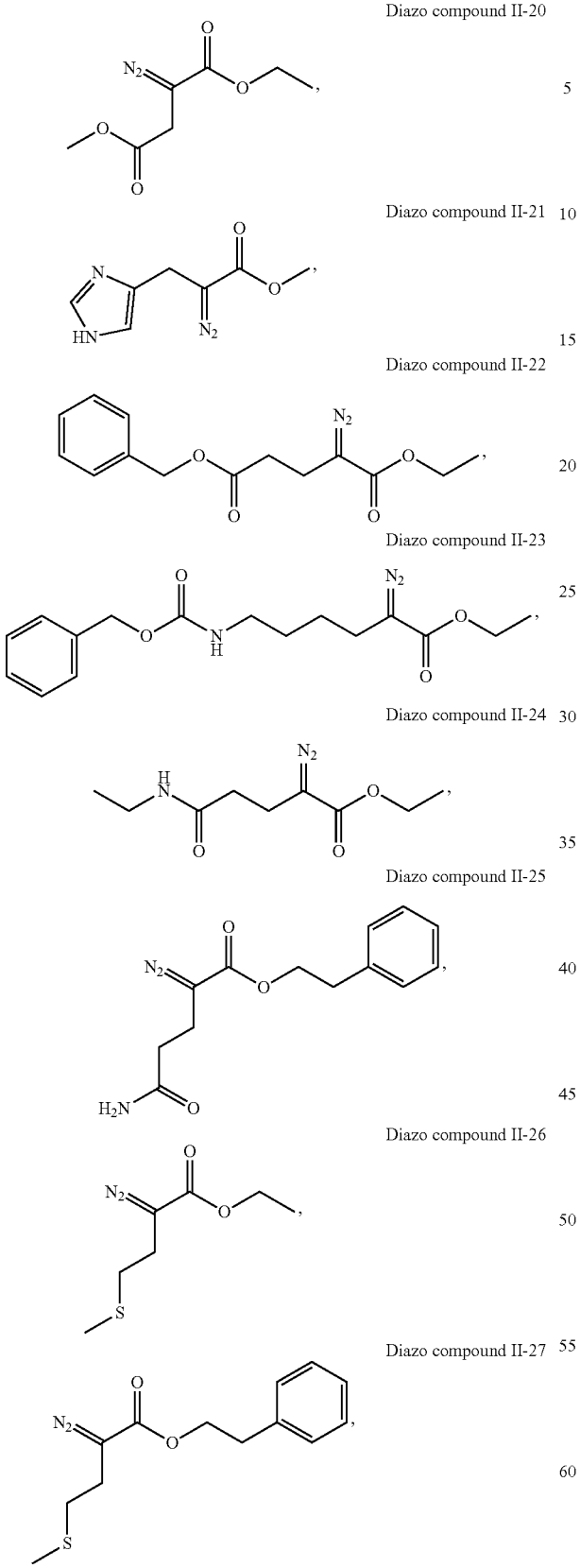
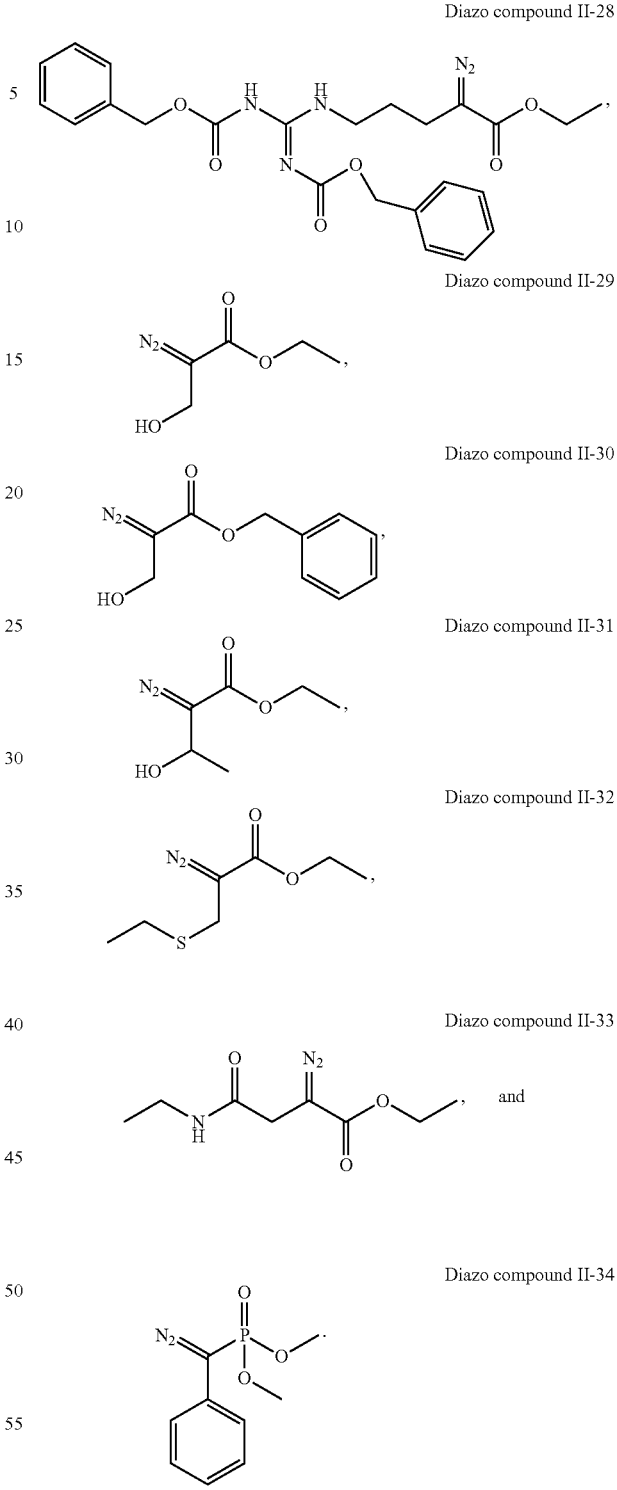
19. The application as claimed in claim 14, wherein a ratio of the equivalents of the basic reagent relative to the equivalents of the N-transfer reagent ranges from 1:1 to 10:1.
* * * * *